US010190175B2

(12) United States Patent
Fach et al.

(10) Patent No.: US 10,190,175 B2
(45) Date of Patent: Jan. 29, 2019

(54) METHOD FOR DETECTING AND IDENTIFYING ENTEROHEMORRHAGIC ESCHERICHIA COLI

(71) Applicants: Agence Nationale de Securite Sanitaire de l'Alimentation, de l'Environnement et du Travail, Maisons-Alfort (FR); Bundesinstitut Fur Risikobewertung, Berlin (DE)

(72) Inventors: Patrick Fach, Charenton le Pont (FR); Sabine Delannoy, Cachan (FR); Lothar Beutin, Berlin (DE)

(73) Assignees: Agence Nationale de Securite Sanitaire de l'Alimentation, de l'Environnement et due Travail, Maisons-Alfort (FR); Bundesinstitut Fur Risikobewertung, Berlin (DE)

(*) Notice: Subject to any disclaimer, the term of this patent is extended or adjusted under 35 U.S.C. 154(b) by 803 days.

(21) Appl. No.: 14/407,884

(22) PCT Filed: Jun. 14, 2013

(86) PCT No.: PCT/IB2013/054888
§ 371 (c)(1),
(2) Date: Dec. 12, 2014

(87) PCT Pub. No.: WO2013/186754
PCT Pub. Date: Dec. 19, 2013

(65) Prior Publication Data
US 2015/0176064 A1    Jun. 25, 2015

(30) Foreign Application Priority Data

Jun. 14, 2012  (EP) .................... 12171941

(51) Int. Cl.
*C12Q 1/68* (2018.01)
*C12Q 1/689* (2018.01)

(52) U.S. Cl.
CPC ....... *C12Q 1/689* (2013.01); *C12Q 2600/156* (2013.01); *C12Q 2600/158* (2013.01)

(58) Field of Classification Search
None
See application file for complete search history.

(56) References Cited

FOREIGN PATENT DOCUMENTS

| EP | 2292799 A1 | 3/2011 |
| WO | 03/062464 A2 | 7/2003 |

OTHER PUBLICATIONS

Vlisidou et al., FEMS micro. lett., 263: 32-40 (2006).*
Arbbeloa, Inf. Imm. 79, 3: 1067-1076, (Mar. 2011).*
Delannoy et al., J. Clin. Microbiol., 50 (11): 3485-3492, (Aug. 15, 2012).*
Written Opinion issued in corresponding International Patent Application No. PCT/IB2013/054888 dated May 12, 2013.
International Search Report issued in corresponding International Patent Application No. PCT/IB2013/054888 dated May 12, 2013.
Bugarel et al., "Identification of Genetic Markers for Differentiation of Shiga Toxin-Producing Enteropathogenic, and Avirulent Strains of *Escherichia coli* O26," Applied and Environmental Microbiology, 77: 2275-2281 (2011).
Bugarel et al., "Virulence gene profiling of enterohemorrhagic (EHEC) and enteropathogenic (EPEC) *Escherichia coli* strains: a basis for molecular risk assessment of typical and atypical EPEC strains," BMC Microbiology, 11: 142 (2011).
Instituto Superiore di Sanita, "Detection and identification of Verocytotoxin-producing *Escherichia coli* (VTEC) O104:H4 in food by Real Time PCR," EU Reference Laboratory for *E. coli*, 1-12 (2011).
Beutin et al., "Evaluation of 'GeneDisc' real-time PCR system for detection of enterohaemorrhagic *Escherichia coli* (EHEC) O26, O103, O111, O145 and O157 strains according to their virulence markers and their O- and H-antigen-associated genes," Journal of Applied Microbiology, 106: 1122-1132 (2009).
Touchon et al., "CRISPR Distribution within the *Escherichia coli* Species Is Not Suggestive of Immunity-Associated Diversifying Selection," Journal of Bacteriology, 193: 2460-2467 (2011).
Grissa et al., "The CRISPRdb database and tools to display CRISPRs and to generate dictionaries of spacers and repeats," BMC Bioinformatics, 8: 172 (2007).
Fabre et al., "CRISPR Typing and Subtyping for Improved Laboratory Surveillance of *Salmonella* Infections," PLoS One, 7: e36995 (2012).

* cited by examiner

*Primary Examiner* — Nancy A Treptow
(74) *Attorney, Agent, or Firm* — Morgan, Lewis & Bockius LLP

(57) ABSTRACT

The invention relates to methods for predicting whether a sample contains enterohemorrhagic *Escherichia coli* (EHEC) of at least one of EHEC O157:[H7], O145:[H28], O103:[H2], O111:[H8], O121:[H19], O26: [H11], O45:[H2] or O104: [H4] serotypes, and for identifying said serotypes, through detection of gene espK in association with at least one of the genetic markers Z1151, Z1153, Z1154, Z1155, Z1156, Z6065, Z2098, ureD or espV and/or through detection of serotype-specific CRISPR sequences.

8 Claims, No Drawings
Specification includes a Sequence Listing.

METHOD FOR DETECTING AND IDENTIFYING ENTEROHEMORRHAGIC *ESCHERICHIA COLI*

SEQUENCE LISTING SUBMISSION VIA EFS-WEB

A computer readable text file, entitled "045636-5271-SequenceListing.txt" created on or about Dec. 9, 2014, with a file size of about 17 kb contains the sequence listing for this application and is hereby incorporated by reference in its entirety.

The invention relates to the identification of Shiga toxin producing *E. coli* (STEC) that constitutes a severe risk for human health.

Shiga toxin-producing *Escherichia coli* (STEC) are a diverse group of *E. coli* belonging to over 400 *E. coli* O:H serotypes, some of which cause outbreaks and sporadic cases of foodborne illness ranging from diarrhoea to hemorrhagic colitis (HC) and the haemolytic uremic syndrome (HUS). According to their human pathogenicity the latter strains were also designated as enterohaemorrhagic *E. coli* (EHEC) (Levine 1987, Nataro and Kaper 1998). Numerous cases of HC and HUS have been attributed to EHEC serotype O157:H7 strains, but it has now been recognized that other serotypes of STEC belong to the EHEC group.

Hence, cumulative evidence from numerous countries indicates that up to 30-60% of human STEC infections are caused by non-O157 STEC and that as few as five to seven "priority" serotypes of STEC are implicated in outbreaks and sporadic cases of HC and HUS. These comprise serotypes O26:[H11], O45:[H2], O103:[H2], O111:[H8], O121:[H19], O145:[H28], O157:[H7] and their non-motile derivatives. In addition, an unusual strain of O104:[H4] has been associated with the largest outbreak of HC and HUS worldwide in 2011 (Scheutz et al., 2011; Frank et al., 2011; Struelens et al., 2011; Gault et al., 2011).

Consequently, many jurisdictions are considering implementation of food inspection programs to safeguard the public from these STEC strains with high virulence for humans. A rational approach for detection of these enterohaemorrhagic *E. coli* (EHEC) strains, as part of a risk-based food inspection program, requires clear definition of the hallmark characteristic of priority STEC (e.g. serogroup, serotypes, virulence and other markers) and effective approaches to detect these pathogenic STEC in foods. Detection of non-O157 EHEC is particularly challenging because, they have no specific characteristics that distinguish them from the large number of harmless commensal *E. coli* that share the same niches. A seropathotype classification has been proposed by Karmali et al. (2003) as a framework to identify the most important O-serogroups involved in food-borne outbreaks, based on severity of disease, frequency and association with outbreaks, but the reasons for the difference in virulence between the various STEC strains remains unclear. It is probable that this difference is due to differences in the pattern of virulence genes possessed by STEC strains and studies are needed to substantiate this and to identify appropriate molecular markers.

Techniques exist to determine the presence of a STEC contamination in a sample by for instance detecting the presence of the stx1/stx2 genes and the eae gene located on the LEE (locus of enterocyte effacement), a locus that was first identified in enteropathogenic *E. coli* (EPEC). But the genetic basis of STEC pathogenicity is a lot more complex than the presence or absence of one or both of these genes. In a complex sample (e.g. food, fecal, environmental samples), which may comprise a mixture of strains (e.g. a mix of STEC and EPEC strains), the presence of the stx1/2 and eae genes is not indicative of the presence of an EHEC in this sample.

However, given that some STEC strains can cause very serious health problems in humans, the detection of a STEC strain in a food product leads to discarding said product, even though it is likely this STEC does not pose a threat to human health. This results in a large amount of wastage due to lack of discrimination between non-pathogenic STEC strains and EHEC strains.

It has been proposed to use, in addition to the stx1/stx2 and eae markers, other genetic markers in order to selectively detect EHEC strains and differentiate them from non-pathogenic STEC strains. For instance, PCT WO 2011/018762 describes a method involving the combined detection of the genes stx1, stx2, eae, nleB and espK to predict the presence of EHEC in a sample.

However, there is still a need of reliable tests allowing a discriminative screening for the presence of EHEC, including non-O157 EHEC, and a specific detection of the EHEC serotypes involved, in particular in case of the "top seven" serotypes O26:[H11], O45:[H2], O103:[H2], O111:[H8], O121:[H19], O145:[H28], O157:[H7].

The inventors have now identified discriminative genetic markers associated with several STEC strains constituting a severe risk for human health. In particular, they have identified genetic markers located within CRISPRs (Clustered Regularly Interspaced Short Palindromic Repeats) sequences of EHEC strains with high virulence for humans.

CRISPRs are present within the genomes of many bacterial species, including *E. coli*. They consist of tandem sequences containing direct repeats of 21 to 47 bp long and separated by spacers of similar size. Spacers are derived from foreign nucleic acids, such as phages or plasmids, and it has been hypothesized that they can protect bacteria from subsequent infection by homologous phages and plasmids.

The inventors have sequenced the CRISPR loci of various EHEC strains which are associated with the world's most frequent clinical cases, and have identified different spacers that can be used for a specific identification of the EHEC serotypes O157:[H7], O145:[H28], O103:[H2], O111:[H8], O121:[H19], O45:[H2], O26:[H11], O104:[H4] and their non motile derivatives, which are responsible for the majority of EHEC infections in humans.

Therefore, an object of the present invention is a method for identifying the serotype(s) of EHEC suspected to be present in a sample, wherein said method comprises detecting the presence or the absence, in said sample or DNA isolated therefrom, of the following *E. coli* CRISPRs sequences:

a) CRISPRs sequences for identifying EHEC O157:[H7] wherein said CRISPRs sequences are selected among:
   the CRISPRs sequences SEQ ID NO: 1, SEQ ID NO: 2, and SEQ ID NO: 3, wherein the presence of one or more of said sequences SEQ ID NO: 1-3 is indicative of the presence of EHEC O157:[H7]; and/or
   the CRISPR sequence SEQ ID NO: 4, wherein the presence of said CRISPR sequence is indicative of the presence of EHEC O157:[H7]; and b) a CRISPR sequence for identifying EHEC O145:[H28], wherein said CRISPR sequence is the sequence SEQ ID NO: 5, and wherein the presence of said CRISPR sequence is indicative of the presence of EHEC O145:[H28]; and c) a CRISPR sequence for identifying EHEC O111:[H8], wherein said CRISPR sequence is the sequence SEQ ID NO:

6, and wherein the presence of said CRISPR sequence is indicative of the presence of EHEC O111:[H8]; and d) a CRISPR sequence for identifying EHEC O121:[H19], wherein said CRISPR sequence is the sequence SEQ ID NO: 7, and wherein the presence of said CRISPR sequence is indicative of the presence of EHEC O121:[H19]; and e) a CRISPR sequence for identifying EHEC O103:[H2] and/or EHEC O45:[H2], wherein said CRISPR sequence is the sequence SEQ ID NO: 8, and wherein the presence of said CRISPR sequence is indicative of the presence of EHEC O103:[H2] and/or of EHEC O45:[H2]; and f) a CRISPR sequence for identifying EHEC O104:[H4], wherein said CRISPR sequence is the sequence SEQ ID NO: 9, and wherein the presence of said CRISPR sequence is indicative of the presence of EHEC O104:[H4]; and g) a CRISPR sequence for identifying EHEC O26:[H11], wherein said CRISPR sequence is the sequence SEQ ID NO: 10, and wherein the presence of said CRISPR sequence is indicative of the presence of EHEC O26:[H11].

According to a preferred embodiment of the invention, said method comprises performing a PCR assay on said sample or DNA isolated therefrom, with primers designed for amplifying said CRISPR sequences, and checking for the presence of the corresponding amplification products.

Preferably, said PCR assay is performed with a combination of primers comprising:

a) primers for detecting EHEC O157:[H7], wherein said primers consist of:
 a set of primers targeting both the CRISPR sequences SEQ ID NO: 1 and SEQ ID NO: 2, wherein said primers are defined by the following sequences:
 GGGAACACAAACCGAAACACA (SEQ ID NO: 11)
 CTTAGTGTGTTCCCCGCGC (SEQ ID NO: 12) and
 a set of primers targeting the CRISPR sequence SEQ ID NO: 3 wherein said primers are defined by the following sequences:
 GAACACTTTGGTGACAGTTTTTGT (SEQ ID NO: 13);
 CTTAGTGTGTTCCCCGCGC (SEQ ID NO: 14),
 wherein the presence of an amplification product for at least one of said sets of primers is indicative of the presence of EHEC O157:[H7]; and/or:
 a set of primers targeting the CRISPR sequence SEQ ID NO: 4, wherein said primers are defined by the following sequences:
 GAACACAAACCGAAACACACG (SEQ ID NO: 15)
 ATAAACCGTCACCAAAACAGTG (SEQ ID NO: 16),
 wherein the presence of an amplification product for said set of primers is indicative of the presence of EHEC O157:[H7]; and b) primers for detecting EHEC O145:[H28], wherein said primers consist of:
 a set of primers targeting the CRISPR sequence SEQ ID NO: 5, wherein said primers are defined by the following sequences:
 GAACTTGAGCCCTGCCAGAA (SEQ ID NO: 17)
 ACCGCGATCTTTTCCTACCTG (SEQ ID NO: 18),
 wherein the presence of an amplification product for said set of primers is indicative of the presence of EHEC O145:[H28]; and c) primers for detecting EHEC O111:[H8], wherein said primers consist of:
 a set of primers targeting the CRISPR sequence SEQ ID NO: 6, wherein said primers are defined by the following sequences:
 GTGACCGCCTGTACACGC (SEQ ID NO: 19)
 CGGATATTTGGGCGTAATACC (SEQ ID NO: 20)
 CTGCCGCGAGTGGTTTCAC (SEQ ID NO: 21),
 wherein the presence of an amplification product for at least one of primers pairs SEQ ID NO: 19 and SEQ ID NO: 20 or SEQ ID NO: 19 and SEQ ID NO: 21 is indicative of the presence of EHEC O111:[H8]; and d) primers for detecting EHEC O121:[H19], wherein said primers consist of:
 a set of primers targeting the CRISPR sequence SEQ ID NO: 7, wherein said primers are defined by the following sequences:
 CGGGGAACACTACAGGAAAGAA (SEQ ID NO: 22)
 GGCGGAATACAGGACGGGTGG (SEQ ID NO: 23),
 wherein the presence of an amplification product for said set of primers is indicative of the presence of EHEC O121:[H19]; and e) primers for detecting EHEC O103:[H2] and/or EHEC O45:[H2], wherein said primers consist of:
 a set of primers targeting the CRISPR sequence SEQ ID NO: 8, wherein said primers are defined by the following sequences:
 GAGTCTATCAGCGACACTACC (SEQ ID NO: 24)
 AACCGCAGCTCGCAGCGC (SEQ ID NO: 25),
 wherein the presence of an amplification product for said set of primers is indicative of the presence of EHEC O103:[H2] and/or of EHEC O45:[H2]; and f) primers for detecting EHEC O104:[H4], wherein said primers consist of:
 a set of primers targeting the CRISPR sequence SEQ ID NO: 9, wherein said primers are defined by the following sequences:
 GGAACTCACCGAGCGCCG (SEQ ID NO: 26);
 GCCTTTGCAGCGTCTTTCCGATC (SEQ ID NO: 27);
 wherein the presence of an amplification product for said set of primers is indicative of the presence of EHEC O104:[H4]; and g) primers for detecting EHEC O26:[H11], wherein said primers consist of:
 two sets of primers targeting the CRISPR sequence SEQ ID NO: 10, wherein the first primers set is defined by the following sequences:
 ACAATCGTGTGTAAATTCGCGG (SEQ ID NO: 28)
 GATAAACCGTGGTACGGAACA (SEQ ID NO: 29)
 and the second said primers set is defined by the following sequences:
 TGAAACCACTCGCGGCAGAT (SEQ ID NO: 30);
 ATAAACCGATCTCCTCATCCTC (SEQ ID NO: 31);
 wherein the presence of an amplification product for at least one of the said sets of primers is indicative of the presence of EHEC O26:[H11].

The amplification products can be detected by any appropriate method for detection of PCR products. For instance, they can be detected by means of probes derived from the respective target sequences.

Examples of preferred probes are given below:
 a probe allowing the detection of amplification products derived from SEQ ID NO: 1 and SEQ ID NO: 2, defined by the following sequence: CGATCAATCCGAATATGAGCGGT (SEQ ID NO: 32), and a probe allowing the detection of amplification products derived from SEQ ID NO: 3, defined by the following sequence: CACTGTTTTGGTGACGGTTTATCC (SEQ ID NO: 33), and/or a probe allowing the detection of amplification products derived from SEQ ID NO: 4, defined by the following sequence: ACAAAAACTGTCACCAAAGTGTTC (SEQ ID NO: 34);

a probe allowing the detection of amplification products derived from SEQ ID NO: 5, defined by the following sequence:
TGGGGCCTCTTTTGTACCCGG (SEQ ID NO: 35);
a probe allowing the detection of amplification products derived from SEQ ID NO: 6, defined by the following sequence:
TGTAATGGCTCACCGGTTTATCCCC (SEQ ID NO: 36);
a probe allowing the detection of amplification products derived from SEQ ID NO: 7, defined by the following sequence:
TCCGCCAACGGCGACAGGGG (SEQ ID NO: 37);
a probe allowing the detection of amplification products derived from SEQ ID NO: 8, defined by the following sequence:
TCGGAACGTGGCGCTATAGGTG (SEQ ID NO: 38);
a probe allowing the detection of amplification products derived from SEQ ID NO: 9, defined by the following sequence:
CTGGGAGGCGTATCTCACGTTCGGT (SEQ ID NO: 39);
a probe allowing the detection of amplification products derived from SEQ ID NO: 10, defined by the following sequence:
TGCTGTCTATATTTCGACCAGTGTTCC (SEQ ID NO: 40);
a probe allowing the detection of amplification products derived from SEQ ID NO: 10, defined by the following sequence:
CCAGCTACCGACAGTAGTGTGTTCC (SEQ ID NO: 41);

According to another aspect of the present invention, it provides a method for predicting whether a sample contains typical enterohemorrhagic *Escherichia coli* (EHEC), (which are defined herein as *Escherichia coli* strains both positive for stx and eae), and/or the atypical EHEC O104:H4 that tested positive for stx and negative for eae. Typical EHEC strains include in particular EHEC O157:H7, O145:H28, O103:H2, O111:H8, O121:H19, O26:H11 and O45:H2 serotypes and their non-motile derivatives.

Said method comprises the detection of the espK gene and of one or more of the following target genes: espy, ureD, Z2098, Z1151, Z1153, Z1154, Z1155, Z1156, and Z6065.

These *E. coli* gene targets correspond to non LEE-encoded type III effectors derived from various genomic O-islands: OI-43, OI-44, OI-50, OI-57 and OI-71.

The combinations of espK with one or more of espV, ureD, Z2098, Z1151, Z1153, Z1154, Z1155, and Z1156, were identified by the inventors among several combinations of putative virulence markers, as being the more predictive of typical EHEC (stx and eae positive *E. coli* strains), and in particular of the presence of EHEC strains of serotypes EHEC O157:[H7], O145:[H28], O103:[H2], O111:[H8], O121:[H19], O26:[H11] or O45:[H2]. The combination of espK with Z6065 is predictive of the presence of the atypical EHEC O104:H4.

Particularly preferred combinations are the following:
espK with one or more of espV, ureD, Z2098;
espK with Z6065;
espK with one or more of espV, ureD, Z2098 and with Z6065.

According to a particular embodiment, said method comprises performing a PCR assay on said sample or DNA isolated therefrom with a combination of primers comprising a set of primers derived from espK and a set of primers derived from at least one of espV, ureD, Z2098, Z1151, Z1153, Z1154, Z1155, Z1156, and Z6065;
and detecting the presence or the absence of an amplification product for each set of primers of said combination.

According to a preferred embodiment of this method, the combination of primers further comprises a set of primers derived from stx1 and a set of primers derived from stx2. This allows screening samples for both the stx genes, as markers of STEC, and for the additional genetic markers listed above, related to priority STEC serotypes that are associated with outbreaks and sporadic cases of HC and HUS.

In contrast to the prior art methods, the method of the invention does not necessitate the detection of the eae gene.

Primers derived from espK, espV, ureD, Z2098, Z1151, Z1153, Z1154, Z1155, Z1156, Z6065, stx1 or stx2 and suitable for use in the PCR assay of the invention, as well as probes allowing the detection of the amplification products obtained with these primers, can easily be designed by one of skill in the art, on the basis of the sequences of these genes available in the databases, for instance within the annotated sequence of *Escherichia coli* O157:H7 (strain EDL933) available in GenBank under accession number AE005174.2.

Non-limitative examples of preferred sets of primers for use in this PCR assay are given below:
a set of primers targeting espK, defined by the following sequences:
GCAGRCATCAAAAGCGAAATCACACC (SEQ ID NO: 42)
TCGTTTGGTAACTGTGGCAGATACTC (SEQ ID NO: 43)
a set of primers targeting espV, defined by the following sequences:
TCAGGTTCCTCGTCTGATGCCGC (SEQ ID NO: 44)
CTGGTTCAGGCCTGGAGCAGTCC (SEQ ID NO: 45)
a set of primers targeting ureD defined by the following sequences:
GCAATAATTGACTCTGATTGCC (SEQ ID NO: 46)
GCTGCTGCGGTAAAATTTACT (SEQ ID NO: 47)
a set of primers targeting Z2098, defined by the following sequences:
CTGAAAAGAGCCAGAACGTGC (SEQ ID NO: 48)
TGCCTAAGATCATTACCCGGAC (SEQ ID NO: 49)
a set of primers targeting Z1153, defined by the following sequences:
CGATCATTGTGGGCATGTTATGCC (SEQ ID NO: 50)
CCTGAATTCACACGGTGATGCG (SEQ ID NO: 51)
a set of primers targeting Z1154, defined by the following sequences:
GCCTTTTTATGTTCATTATTGCGGTTG (SEQ ID NO: 52)
GTATAGTTTTAGCAATACCTTCCTGC (SEQ ID NO: 53)
a set of primers targeting Z1155, defined by the following sequences:
GATTGTGGCGATTAATGGGGG (SEQ ID NO: 54)
ACACCGATCTGGTCATTGGCG (SEQ ID NO: 55)
a set of primers targeting Z1156, defined by the following sequences:
AAACGCCTTTAAAATCTGCGTCT (SEQ ID NO: 56)
TGCCGTGCGCACAGTCATAAG (SEQ ID NO: 57)
a set of primers targeting Z1151, defined by the following sequences:
GCCCATGGCTCCACATCCTG (SEQ ID NO: 58)

CCAAAAAAGTTATGATGATTGCACTG (SEQ ID NO: 59)

a set of primers targeting Z6065, defined by the following sequences:
GCACTGGCCCTTGTTGCTCAGGC (SEQ ID NO: 60)
GCTCTTCCAGTGAGAATGTCTTTCCGG (SEQ ID NO: 61)

a set of primers targeting stx1 and stx2, defined by the following sequences:
TTTGTYACTGTSACAGCWGAAGCYTTACG (SEQ ID NO: 62)
CCCCAGTTCARWGTRAGRTCMACRTC (SEQ ID NO: 63)

Non-limitative examples of probes for detecting the amplification products are given bellow:

a probe allowing the detection of amplification products derived from espK, defined by the following sequence:
ATTCAGATAGAAGAAGCGCGGGCCAG (SEQ ID NO: 64);

a probe allowing the detection of amplification products derived from espy, defined by the following sequence:
CTTGCAACACGTTACGCTGCCGAGTATT (SEQ ID NO: 65);

a probe allowing the detection of amplification products derived from UreD, defined by the following sequence:
TACGCTGATCACCATGCCTGGTGC (SEQ ID NO: 66);

a probe allowing the detection of amplification products derived from Z2098, defined by the following sequence:
TAACTGCTATACCTCCGCGCCG (SEQ ID NO: 67);

a probe allowing the detection of amplification products derived from Z1153, defined by the following sequence:
TGTAACACCCAGACGGTCAGCAACATG (SEQ ID NO: 68);

a probe allowing the detection of amplification products derived from Z1154, defined by the following sequence:
TCACTTCCAGTTTCTGGTGATGTTTTGAT (SEQ ID NO: 69);

a probe allowing the detection of amplification products derived from Z1155, defined by the following sequence:
TGGGTGAGGTTAAAATATAAAGAACGATTGC (SEQ ID NO: 70);

a probe allowing the detection of amplification products derived from Z1156, defined by the following sequence:
TAAGATATTTCTGACTTTCCGCATGCGCTT (SEQ ID NO: 71);

a probe allowing the detection of amplification products derived from Z1151, defined by the following sequence:
AAAGAGCCAGCGCAGAGCTGACCAG (SEQ ID NO: 72);

a probe allowing the detection of amplification products derived from Z6065, defined by the following sequence:
TTCGCTGGAAGCAGAGCCCGTGC (SEQ ID NO: 73);

a probe allowing the detection of amplification products derived from stx1, defined by the following sequence:
CTGGATGATCTCAGTGGGCGTTCTTATGTAA (SEQ ID NO: 74);

a probe allowing the detection of amplification products derived from stx2, defined by the following sequence:
TCGTCAGGCACTGTCTGAAACTGCTCC (SEQ ID NO: 75);

Advantageously, the invention provides a method for predicting whether a sample contains typical enterohemorrhagic *Escherichia coli* (EHEC) of at least one of EHEC O157:[H7], O145:[H28], O103:[H2], O111:[H8], O121:[H19], O26:[H11] and O45:[H2] serotypes, and further identifying the serotype(s) of said EHEC, wherein said method comprises:

performing a PCR assay for assessing whether or not said sample comprises EHEC of at least one of O157:[H7], O145:[H28], O103:[H2], O111:[H8], O121:[H19], O26:[H11], O45:[H2] and O104:H4 serotypes, as described above, and if the results of said PCR assay are positive, performing a PCR assay for identifying the serotype(s) of said EHEC, as described above.

The PCR assays of the invention can be used for testing any sample of a substance potentially containing EHEC, such as food samples, water samples, soil samples, etc.

The PCR assays of the invention can be carried out using any method suitable for PCR amplification of target sequences, using any of the various natural or engineered enzymes available for this purpose. Alternative methods such as nucleic acid sequence-based amplification (NASBA), branched DNA, strand displacement amplification or the loop-mediated isothermal amplification (LAMP) method (Compton 1991, Chang 1991, Walker et al. 1992, Notomi et al., 2000) can also be used.

Particularly preferred methods are those involving real time PCR amplification as described by Ian M. Mackay in "Real-time PCR in Microbiology: from diagnosis to characterization" (2007) Caister Academic Press, Norfolk, UK.

Real time PCR, also called quantitative real time polymerase chain reaction (qPCR) or kinetic polymerase chain reaction, is used to amplify and simultaneously quantify a targeted DNA molecule. It enables both detection and quantification (as absolute number of copies or relative amount when normalized to DNA input or additional normalizing genes) of a specific sequence in a DNA sample. The procedure follows the general principle of polymerase chain reaction; its key feature is that the amplified DNA is quantified as it accumulates in the reaction in real time after each amplification cycle (Mackay 2007). Two common methods of quantification are the use of fluorescent dyes that intercalate with double-strand DNA, and modified DNA oligonucleotide probes that fluoresce when hybridized with a complementary DNA (Mackay 2007). In the present invention the inventors have shown the second of these two methods, but the other method of quantifying PCR products based upon intercalating fluorescent dyes is also within the scope of the present invention.

Non-limiting examples of suitable fluorescent labels include 6-carboxyl-fluorescein (FAM), tetrachloro-6-carboxyfluorescein (TET), 6-carboxy-X-rhodamine (ROX). Non-limitative examples of suitable quenchers for labelling dual-labelled probes include 6-carboxy-tetramethyl-rhodamine (TAMRA), DABCYL, Non-Fluorescent Quenchers such as quenchers of the Black Hole Quencher family (BHQ), or including a minor groove binder group (MGB).

Each of the PCR assays of the invention can be carried out by performing a separate PCR reaction for each target sequence to be detected (simplex PCR). However, in many cases it will be preferred to carry out multiplex PCR, allowing amplification of several target sequences in a single reaction. Advantageously, one can use a macroarray, i.e. a preformed structure such as a substrate upon which the desired DNA primers have been spotted. Such a macroarray allows the routine performance of multiplex PCR assays described herein. By way of example, one can use the GeneDisc® macroarray (Pall-GeneDisc Technology, Bruz, France) described for instance by Beutin et al. (Beutin et al. 2009) which allows the simultaneous detection of multiple targets in reaction microchambers preloaded with the reagents necessary for detecting and quantifying the required targets.

In order to ensure that the results of the assay are representative of the true contents of the sample, it may also comprise a negative amplification control to ensure any detected products are true positives and also an inhibition control to ensure that the DNA from the sample is able to be amplified and hence that no false negatives are generated.

The invention also encompasses the primer sets and the probes defined above, allowing carrying out the PCR assays of the invention, as well as kits associating these primer sets and these probes, eventually associated with reagents to perform a PCR reaction. These kits may also comprise instructions for performing said amplification reaction. The amplification products using the primers of the invention are also part of the invention.

According to a first embodiment, a kit of the invention comprises a combination of primers comprising:
  a set of primers defined by the sequences SEQ ID NO: 11 and SEQ ID NO: 12 and a set of primers defined by the sequences SEQ ID NO: 13 and SEQ ID NO: 14, and/or a set of primers defined by the sequences SEQ ID NO: 15 and SEQ ID NO: 16;
  a set of primers defined by the sequences SEQ ID NO: 17 and SEQ ID NO: 18;
  a set of primers defined by the sequences SEQ ID NO: 19, SEQ ID NO: 20, and SEQ ID NO: 21;
  a set of primers defined by the sequences SEQ ID NO: 22 and SEQ ID NO: 23;
  a set of primers defined by the sequences SEQ ID NO: 24 and SEQ ID NO: 25;
  a set of primers defined by the sequences SEQ ID NO: 26 and SEQ ID NO: 27;
  a set of primers defined by the sequences SEQ ID NO: 28 and SEQ ID NO: 29;
  a set of primers defined by the sequences SEQ ID NO: 30 and SEQ ID NO: 31;
  Preferably, said kit also comprises:
  a probe allowing the detection of amplification products derived from SEQ ID NO: 1 and SEQ ID NO: 2, and a probe allowing the detection of amplification products derived from SEQ ID NO: 3, and/or a probe allowing the detection of amplification products derived from SEQ ID NO: 4, as defined above;
  a probe allowing the detection of amplification products derived from SEQ ID NO: 5, as defined above;
  a probe allowing the detection of amplification products derived from SEQ ID NO: 6, as defined above;
  a probe allowing the detection of amplification products derived from SEQ ID NO: 7, as defined above;
  a probe allowing the detection of amplification products derived from SEQ ID NO: 8, as defined above;
  a probe allowing the detection of amplification products derived from SEQ ID NO: 9, as defined above;
  two probes allowing the detection of amplification products derived from SEQ ID NO: 10, as defined above.

According to a second embodiment, a kit of the invention comprises:
  a set of primers derived from espK, and
  one or more set(s) of primers selected among: a set of primers derived from espV, a set of primers derived from ureD, a set of primers derived from Z2098, a set of primers derived from Z1151, a set of primers derived from Z1153, a set of primers derived from Z1154, a set of primers derived from Z1155, a set of primers derived from Z1156, a set of primers derived from Z6065.

Preferably, said kit also comprises a probe allowing the detection of amplification products derived from espK, and one or more probe(s) selected among: a probe allowing the detection of amplification products derived from espV, a probe allowing the detection of amplification products derived from ureD, or a probe allowing the detection of amplification products derived from Z2098, a probe allowing the detection of amplification products derived from Z1151, a probe allowing the detection of amplification products derived from Z1153, a probe allowing the detection of amplification products derived from Z1154, a probe allowing the detection of amplification products derived from Z1155, a probe allowing the detection of amplification products derived from Z1156, a probe allowing the detection of amplification products derived from Z6065.

The kits according to the second embodiment described above may further comprise a set of primers targeting stx1 and a set of primers targeting stx2, and preferably a probe allowing the detection of amplification products derived from stx1, and a probe allowing the detection of amplification products derived from stx2.

For a better understanding of the invention and to show how the same may be carried into effect, there will now be shown by way of example only, specific embodiments, methods and processes according to the present invention.

EXAMPLE 1: IDENTIFICATION OF DNA SEQUENCES DERIVED FROM THE CRISPRS LOCI OF *E. COLI* FOR SPECIFIC IDENTIFICATION OF ENTEROHAEMORRHAGIC *E. COLI* (EHEC)

Materials and Methods

Bacterial Strains

Strains of *E. coli* (n=955) that were investigated for their CRISPR loci by high throughput real-time PCR are reported in Table I below.

TABLE I

*E. coli* strains

EHEC* (n = 331)

O103:[H25] (n = 6), O103:H2 (n = 38), O111:H8 (n = 49), O118:[H16] (n = 3), O119:[H25] (n = 4), O121:H19 (n = 12), O123:H11, O127:H8s, O145, O145:[H28] (n = 29), O156:H21, O156:H25 (n = 10), O157:[H7] (n = 75), O165:H25, O172:[H25], O172:H25, O172:NM, O177 (n = 2), O177:[H25], O182:[H25], O26:[H11] (n = 76), O3, O45:H2, O49:H16, O5 (n = 8), O55, O76:H51, O84:H2, Ont:[H2], Or:H16, OX186:[H2]

TABLE I-continued

E. coli strains

EPEC (n = 344)

O100:[H25] (n = 2), O102:H19, O103:H21, O103:H8, O108:H9 (n = 6), O109:H25, O111, O111:B4,
O111:H11, O111:H19 (n = 3), O111:H2 (n = 13), O111:H25 (n = 2), O111:H47, O111:H9 (n = 3), O113:H6 (n = 2),
O114:H2 (n = 6), O114:H49 (n = 5), O115:H38 (n = 3), O117:H25, O117:H40b (n = 3), O118:H5, O118:H8a
(n = 3), O119:[H25], O119:H2 (n = 3), O119:H6 (n = 4), O119:H8 (n = 2), O119:H9, O119s:H2, O123/O4:H45
(n = 2), O123:H25, O125:H6, O125ac:H6 (n = 3), O126:H27, O126:H6, O127, O127:H19, O127:H40 (n = 4),
O127:H40b (n = 2), O127:H6 (n = 2), O128:[H2] (n = 12), O128:H8, O128ac:H2, O142:H34, O142:H6 (n = 3),
O145:H34 (n = 5), O15:H11, O15:H2 (n = 3), O153:H14, O156, O156:[H8] (n = 7), O156:H1 (n = 2), O156:H25
(n = 3), O157, O157:[H45] (n = 2), O157:H16 (n = 5), O157:H2, O157:H26 (n = 2), O157:H39, O157:H45 (n = 3),
O177:H26, O186:[H45], O2:[H40] (n = 2), O2:H40b, O2:H8, O21:H25, O22:H7, O26:[H11] (n = 38), O26:H31,
O26:H34, O28:H28 (n = 4), O3:H40b, O3:H5, O3:H8a (n = 3), O37:H10, O4:H16, O45, O45:H7, O45:H9,
O49:[H10] (n = 2), O49:H—, O5:H11, O51:H49 (n = 3), O55:[H51], O55:[H7] (n = 26), O55:H6 (n = 5), O62:H9,
O63:H6 (n = 2), O66:H8/8a, O69:[H2], O69:H16 (n = 2), O70/O86:H2, O70:H11 (n = 5), O71:H40b, O76:H41,
O76:H7 (n = 5), O80:[H2] (n = 3), O84:[H2], O86:[H34] (n = 4), O86:H11 (n = 2), O86:H40, O86:H8 (n = 4),
O86:H8a, O88:H8a, O89:[H2], O9:H10, OK8:H10, Ont:[H10], Ont:[H6], Ont:H11, Ont:H14, Ont:H2 (n = 2),
Ont:H21, Or:H40b, Or:H8a, Or:H9, OX177:H11 (n = 2), OX177:H6

STEC** (n = 160)

O100:NM (n = 2), O101:H— (n = 3), O104:H7, O105:H18, O109:H—, O110:H28, O111, O111:H10, O113:H4,
O115:H18 (n = 2), O116:H28, O117 (n = 2), O117:H7 (n = 2), O118:H12 (n = 3), O125, O126, O126:H8,
O128ab:H2, O130:H11, O136 (n = 2), O138, O139, O139:H1, O141:[H4], O141ac, O146:H21, O146:H28
(n = 2), O146:H8, O147, O149:H19, O15:H16, O153:H25 (n = 3), O165:H11, O168:H8, O17/77:H41, O171:H—,
O171:H2, O172:H21, O174:[H21] (n = 11), O174:H2, O174:H8 (n = 4), 0176:H—, O178:H19, O179:H8,
O181:H49, O2:H25, O2:H27, O21:H21 (n = 3), O22/O83, O22:H16 (n = 2), O22:H8 (n = 3), O23:H15, O3,
O39:H48, O40:21, O40:H8, O46:H38 (n = 2), O48:H21, O5, O5:[H19], O53, O6 (n = 7), O6:H10 (n = 2), O6:H34
(n = 2), O68:H12, O73:H18, O74:H42, O75:H8, O76, O76:H19 (n = 3), O77 (n = 2), O79, O79:H48, O8:H10,
O8:H19 (n = 6), O8:H8, O85:H11, O86, O88:H25, O91 (n = 6), O91:[H21] (n = 5), O91:H10 (n = 3), O91:H14
(n = 2), O92, O107:H—, O92, O107:H48, O96:H19, Ont:H—, Ont:H7, Or:[H16], Or:H12, Or:H29, Or:H33, Or:H4,
Or:H48, OX178:H19, OX185:H28, OX187:Hbev, OX3:H—, OX3:H2, OX3:H21, OX7:H16

Apathogenic E. coli (n = 120)

O103 (n = 2), O103:H8, O104:H7, O110, O111:H12, O111:H21, O121:[H45], O126 (n = 33), O126:H11,
O126:H27 (n = 3), O127 (n = 8), O127:H10, O127:H21, O142 (n = 8), O145:H2 (n = 2), O150:H8, O153:H12,
O156:H33, O156:H47, O156:H56, O157 (n = 5), O157:H27, O180:H—, O26:H? (n = 4), O26:H21/32, O26:H32
(n = 6), O26:NM, O4:H5, O41:H7, O45:H7, O55 (n = 8), O55:H19, O55:H21, O6:H4, O62:H30 (n = 2),
O8/O104:H10, O8/O104:H45, O86 (n = 6), O86/O125ac, O86:H2, O86:H27, O88, O9:K9:H12, OX183:H18

For each serotype, n = 1 unless otherwise stated.
*Including EHEC derivatives as described in (Bugarel et al. 2010).
**Including atypical EHEC.

E. coli strains were divided into Shiga-toxin producing E. coli or STEC (n=160), enteropathogenic E. coli or EPEC (n=344), enterohaemorrhagic E. coli or EHEC (n=331) and apathogenic E. coli (n=120). The STEC/EHEC type was defined on the presence of stx- and eae-genes. EHEC strains were defined as harbouring both a stx gene (stx1 and/or stx2) and eae, while STEC strains harboured stx only. STEC included stx-positive and eae-negative E. coli strains of serotypes O91:[H21], O113:[H21], O104:[H21], also named atypical EHEC, which are less frequently involved in hemorrhagic diseases than other EHEC, but are a frequent cause of diarrhea. Stx-negative derivatives of EHEC strains were designated as EHEC-like and were defined based on their nle gene profile, eae subtype and serotype as described by Bugarel et al. (2010; 2011) except for the EHEC-like strains of serotype O26:H11 which were identified based on the presence of the gene espK and their allelic type 2 of the arcA gene (Bugarel et al., 2011). EPEC strains were defined as described by Bugarel et al. (2011). Apathogenic E. coli were defined as stx- and eae-negative strains.

All strains investigated in this work were identified for the E. coli O (LPS) and H (flagellar) antigens and have been characterized for the stx- and eae-genes as previously reported (Bugarel et al. 2010). For examination, bacteria were cultured to single colonies on Luria-Broth Plates and grown overnight at 37° C. One colony was picked-up and DNA extracted using the InstaGene matrix (Bio-Rad Laboratories, Marnes La Coquette, France) before high throughput real-time PCR testing.

DNA Sequencing

The CRISPR loci of E. coli strains were PCR amplified with the primers listed in Table II. The double stranded DNA sequencing of the CRISPR amplicons was performed by Eurofins MWG Operon (Courtaboeuf, France) using the sequencing primers listed in Table II.

TABLE II

| Primer name | Forward primer and reverse primer sequences (5'-3') | SEQ ID NO: | Accession Number | Location within sequence |
|---|---|---|---|---|
| CRISPR-I-F | GGTGAAGGAGYT GGCGAAGGCGTC | 76 | AE005174 | 3665412-3665435 |
| CRISPR-I-R | CCGGTGGATTTG GATGGGTTACG | 77 | AE005174 | 3665885-3665863 |
| CRISPR-II-F | TGTGAACCTCTC TGGCATGGAG | 78 | AP010953 | 3786919-3786940 |
| CRISPR-II-R | TAAAGTTGGTAG ATTGTGACTGGC | 79 | AP010953 | 3787672-3787649 |

High-Throughput Real-Time PCR

The LightCycler® 1536 (Roche, Meylan, France) was used to perform high-throughput real-time PCR amplifications. For the PCR setup of the LightCycler® 1536 multi-well plates, the Bravo liquid dispenser automat (Agilent Technologies, Massy, France) equipped with a chiller and the PlateLoc thermal microplate sealer (Agilent Technologies) were used. The PCR reactions contained 0.5 µl sample and 1 µl master mix containing 1× RealTime ready DNA Probes master (Roche) (corresponding to 0.7× final), 300 nM each primer and 300 nM each probe (corresponding to 200 nM final each). Amplifications were performed using FAM- or HEX-labeled TaqMan® probes. Primers and probes used for PCR amplifications are listed in Table III. The LightCycler® 1536 real-time PCR system was used with the following thermal profile: 95° C. for 1 min followed by 35 cycles of 95° C. for 0 s (ramp: 4.8° C./s) and 60° C. for 30 s (ramp: 2.5° C./s) and a final cooling step at 40° C. for 30 s. The software settings were Dual color hydrolysis probes/UPL probes and Master Control.

Results

Identification of Specific DNA Sequences Targeting the CRISPRs Loci of EHEC O157:H7

Sequencing the CRISPR loci of various EHEC O157:[H7] strains has shown the polymorphism of this locus for this serotype. Sequences characteristic of the CRISPR loci of EHEC O157:[H7] strains are reported in SEQ ID NO: 1, 2, 3 and 4. Based on these sequences and the CRISPR locus of the strain EDL933 (Accession number AE005174), various real-time PCR assays were designed (SP_O157_A, SP_O157_B and SP_O157_C) for detecting EHEC O157:[H7]. The specificity and sensitivity of the assays was tested against a panel of 955 *E. coli* strains, including 75 strains of EHEC O157:[H7] (Table I). The PCR tests proved to be highly sensitive and specific for EHEC O157:[H7]. Sensitivity of the assays was ranging from 92.0% to 97.3% with only few O157:[H7] strains being not detected by each assay. The specificity of the PCR tests was high, ranging from 99.6 to 100%. The PCR assay SP_O157_B was the

TABLE III

| | Forward primer, reverse primer and probe sequences (5'-3') | SEQ ID NO: | Target sequence |
|---|---|---|---|
| SP_O157_A | GAACACAAACCGAAACACACG<br>ATAAACCGTCACCAAAACAGTG<br>[FAM]-ACAAAAACTGTCACCA AAGTGTTC-[BHQ1] | 15<br>16<br>34 | (SEQ ID NO: 4) |
| SP_O157_B | GGGAACACAAACCGAAACACA<br>CTTAGTGTGTTCCCCGCGC<br>[HEX]-CGATCAATCCGAATATGA GCGGT-[BHQ1] | 11<br>12<br>32 | (SEQ ID NO: 1 and 2) |
| SP_O157_C | GAACACTTTGGTGACAGTTTTTGT<br>CTTAGTGTGTTCCCCGCGC<br>[HEX]-CACTGTTTTGGTGACGGT TTATCC-[BHQ1] | 13<br>14<br>33 | (SEQ ID NO: 3) |
| SP_O121 | CGGGGAACACTACAGGAAAGAA<br>GGCGGAATACAGGACGGGTGG<br>[HEX]-TCCGCCAACGGCGACA GGGG-[BHQ1] | 22<br>23<br>37 | (SEQ ID NO: 7) |
| SP_O45 | GAGTCTATCAGCGACACTACC<br>AACCGCAGCTCGCAGCGC<br>[HEX]-TCGGAACGTGGCGCT ATAGGTG-[BHQ1] | 24<br>25<br>38 | (SEQ ID NO: 8) |
| SP_O145 | GAACTTGAGCCCTGCCAGAA<br>ACCGCGATCTTTTCCTACCTG<br>[HEX]-CTGGGAGGCGTATCTC ACGTTCGGT-[BHQ1] | 17<br>18<br>35 | (SEQ ID NO: 5) |
| SP_O104 | GGAACTCACCGAGCGCCG<br>GCCTTTGCAGCGTCTTTCCGATC<br>[HEX]-CTGGGAGGCGTATCT CACGTTCGGT-[BHQ1] | 26<br>27<br>39 | (SEQ ID NO: 9) |
| SP_O26_C | ACAATCGTGTGTAAATTCGCGG<br>GATAAACCGTGGTACGGAACA<br>[HEX]-TGCTGTCTATATTTCG ACCAGTGTTCC-[BHQ1] | 28<br>29<br>40 | (SEQ ID NO: 10) |
| SP_O26_D | TGAAACCACTCGCGGCAGAT<br>ATAAACCGATCTCCTCATCCTC<br>[HEX]-CCAGCTACCGACAGTAG TGTGTTCC-[BHQ1] | 30<br>31<br>41 | (SEQ ID NO: 10) |
| SP_O111 | GTGACCGCCTGTACACGC<br>CGGATATTTGGGCGTAATACC<br>CTGCCGCGAGTGGTTTCAC<br>[HEX]-TGTAATGGCTCACCG GTTTATCCCC-[BHQ1] | 19<br>20<br>21<br>36 | (SEQ ID NO: 6) | unique test giving cross reaction with very few strains of serogroup O55. By combining the PCR assays SP_O157_B and SP_O157_C all the 75 EHEC O157:[H7] strains were correctly detected (100% sensitivity) and only 3 isolates of serogroup O55 were cross-reacting (99.6% specificity).

Identification of Specific DNA Sequences Targeting the CRISPR Locus of EHEC O145:H28

The CRISPR locus of EHEC O145:[H28] has been characterized (SEQ ID NO: 5) by sequencing one of the two CRISPR loci identified in *E. coli*. A PCR assay (SP_O145) has been designed from this CRISPR sequence to target EHEC O145:[H28]. Among the 955 *E. coli* strains that were investigated with this PCR test, only the 29 EHEC O145:[H28] and 4 EPEC O28:H28 strains were tested positive. Sensitivity and specificity of the PCR assay SP_O145 were respectively of 100% and 99.5%.

Identification of Specific DNA Sequences Targeting the CRISPR Locus of EHEC O111:H8

Based on the sequence of the CRISPR locus of EHEC O111:H8, (SEQ ID NO: 6), a real-time PCR assay has been designed (SP_O111) to detect EHEC O111:[H8]. Investigation of 980 *E. coli* strains by the PCR assay SP_O111 gave positive results for 47 EHEC O111:[H8] out of the 49 O111:[H8] strains tested. Only one EPEC strain of serotype O45:H7 was tested positive. Sensitivity and specificity of this PCR assay were high, 95.9% and 99.9% respectively.

Identification of Specific DNA Sequences Targeting the CRISPR Locus of EHEC O121:H19

The CRISPR locus of EHEC O121:[H19] has been sequenced in this study (SEQ ID NO: 7). A PCR assay (SP_O121) has been designed from this sequence to target EHEC O121:[H19]. Among the 955 *E. coli* strains tested by the PCR assay SP_O121, only one O104:H7 and the 12 EHEC O121:[H19] strains were tested positive, showing that this PCR test was highly sensitive (100%) and specific (99.9%).

Identification of Specific DNA Sequences Targeting the CRISPRs Loci of EHEC O103:H2 and O45:H2

Based on the sequence determination of the CRISPR locus of EHEC O45:[H2] (SEQ ID NO: 8) and the sequence of the CRISPR locus of EHEC O103:H2, issued from strain 12009 (accession number AP010958), a PCR assay (SP_O45) has been designed and tested positive one strain of EHEC O45:H2 and all the 38 EHEC O103:H2 strains investigated in this study. Thus, the PCR assay SP_O45 has shown high sensitivity (100%) for EHEC O103:[H2] and O45:[H2]. This test has 98.6% specificity when tested on a large panel of *E. coli*, giving only minor cross-reactions with few strains of the following serotypes: O118:H8, O128:[H2], O128:H8, O128:H2, O89:[H2], O46:H38, O8:H8, O142, O145:H2 and one O103 strain that tested negative for the flagella H2.

Identification of Specific DNA Sequences Targeting the CRISPR Locus of EHEC O104:H4

The CRISPR locus of EHEC O104:[H4] has been sequenced in this study (SEQ ID NO: 9). A PCR assay (SP_O104) has been designed from this sequence to target EHEC O104:[H4]. The PCR assay targeting the CRISPR locus of *E. coli* O104:H4 has been evaluated on a panel of 1303 strains of *E. coli* that included the 186 known O-serogroups and 56 H-types. This PCR assay gave positive results for the 48 O104:H4 isolates (including one Or:H4 isolate) related to the outbreak occurring in May 2011, and to one O104:H4 clinical isolate reported in 2001. The 39 strains of *E. coli* O104 having other H-types than H4 were tested negative. The *E. coli* strains carrying a K9 capsular antigen (O8:K9:H10, O8:K9:H45, O9:K9:H1, O9:K9:H12 and O9:K9:H51) which cross react by agglutination with the sera anti-O104 tested all negative. In final, among the other *E. coli* strains that included the 186 known O-serogroups and 56 H-types, only 5 isolates belonging to serotypes Ont:H2, O43:H2, O141:H2, and O174:H2 were cross reacting with the primers and probes designed in the CRISPR locus of EHEC O104:H4. Additional O174:H2, O141:H2 and O43:H2 strains were thus tested for CRISPR-O104. Three out of twelve O174:H2 tested positive, as well as ¾ O43:H2 and ⅛ O141:H2. All together the data showed that that this PCR test was highly sensitive (100%) and specific (99.6%).

Identification of Specific DNA Sequences Targeting the CRISPR Locus of EHEC O26:H11

Sequencing the CRISPR loci of various EHEC O26:[H11] strains has shown the polymorphism of this locus for this serotype. A Sequence characteristic of the CRISPR loci of EHEC O26:[H11] is reported in SEQ ID NO: 10. Based on these sequences and the CRISPR locus of the EHEC O26:H11 strain 11368 (Accession numbers AP010953, NC_013361), two real-time PCR assays were designed (SP_O26_C, and SP_O26_D) for detecting EHEC O26:[H11]. The specificity and sensitivity of the assays was tested against a panel of 980 *E. coli* strains, including 77 strains of EHEC O26:[H11] and EHEC-like O26:[H11]. The two PCR tests proved to be sensitive and specific for EHEC O26:[H11]. Sensitivity of the SP_O26_C PCR assay was 87.0% whereas the sensitivity of SP_O26_D PCR assay was 90.9%. Only few O26:[H11] strains were not detected by each assay. The specificity of the PCR test SP_O26_C was 98.7% (12 strains cross-reacting) whereas the specificity of the PCR test SP_O26_D was 98.1% (17 strains cross-reacting). By combining the PCR assays SP_O26_C and SP_O26_D only 4 EHEC-like O26:H11 strains out of the 77 EHEC-like and EHEC O26:[H11] strains were not detected (94.8% sensitivity) and only 26 *E. coli* were cross-reacting (97.1% specificity).

Conclusion:

The results of this study are summarized in Table IV below.

TABLE IV

| | | | Sensitivity and specificity | | |
|---|---|---|---|---|---|
| Serotype | Number | PCR | Sensitivity | Specificity | Cross-reaction |
| O157:[H7][a] | 75 | SP_O157_A | 92.0% | 100% | — |
| | | SP_O157_B | 97.3% | 99.6% | O55:[H7][a], O55:[H7] (n = 2)[b] |
| | | SP_O157_C | 94.7% | 100% | — |
| | | SP_O157_B + C | 100% | 99.6% | O55:[H7][a], O55:[H7] (n = 2)[b] |
| O103:H2[a], O45:H2[a] | 38 1 | SP_O45 | 100% | 98.6% | O118:H8a (n = 3)[b], O128:[H2][b], O128:H8[b], O128ac:H2[b], O89:[H2][b], O46:H38[c], O8:H8[c], O103[d], O142[d], O145:H2[d] |

TABLE IV-continued

Sensitivity and specificity

| Serotype | Number | PCR | Sensitivity | Specificity | Cross-reaction |
|---|---|---|---|---|---|
| O111:H8[a] | 49 | SP_O111 | 95.9% | 99.9% | O45:H7 (n = 1)[b] |
| O121:H19[a] | 12 | SP_O121 | 100% | 99.9% | O104:H7[d] |
| O145:[H28][a] | 29 | SP_O145 | 100% | 99.5% | O28:H28 (n = 4)[b] |
| O104:[H4][a] | 49 | SP_O104 | 100% | 99.6% | Ont:H2, O43:H2 (n = 4), O141:H2 (n = 2), and O174:H2 (n = 4) |
| O26:[H11][a] | 77 | SP_O26_C | 87% | 98.7% | O111:H11[b], O111:H47[b], O118:H16 (n = 2)[a], O118:H8a (n = 3)[b], O128:H8[b], O26:H11[b], O118:H2[a], O103:H11[a], O111[b] |
| | | SP_O26_D | 90.9% | 98.1% | O118:H16 (n = 3)[a], O123:H11[a], O26:H11 (n = 9)[b], O118:H2 (n = 2)[a], O86:H11 (n = 2)[b], O103:H11[a] |
| | | SP_O26_C + D | 94.8% | 97.1% | O111:H11[b], O111:H47[b], O118:H16 (n = 4)[a], O118:H8a (n = 3)[b], O123:H11[a], O128:H8[b], O26:H11 (n = 10)[b], O86:H11 (n = 2)[b], O118:H2 (n = 2)[a], O103:H11[a], O111[b] |

For each serotype, n = 1 unless otherwise stated.
[a]EHEC & EHEC-like;
[b]EPEC;
[c]STEC & atypical EHEC;
[d]non pathogenic E. coli Sequencing the CRISPR loci of various EHEC strains has shown the genetic diversity of the CRISPR sequences issued from EHEC associated with the world's most frequent clinical cases. Analysis of the spacer sequences located between the short palindromic repeat sequences of the CRISPR loci, allowed identifying useful genetic markers to detect with high sensitivity and specificity EHEC strains. Based on a high-throughput real-time PCR approach, a very large panel of E. coli strains, that comprised EHEC, EPEC, STEC and apathogenic E. coli was investigated with regards to their CRISPR loci content. In final, EHEC O145:H28 (n=29), O103:H2 (n=38), O121:H19 (n=12), O104:H4 (n=49) and O45:H2 (n=1) were detected with 100% sensitivity with each PCR assays targeting various CRISPR sequences derived from these EHEC serotypes. EHEC O157:[H7] (n=75) was detected with 100% sensitivity when combining the PCR assays SP_O157_B and SP_O157_C which target two different sequences of the EHEC O157 CRISPR loci. EHEC O111:[H8] (n=49) was detected with 95.9% sensitivity (47/49 O111:[H8] were detected, only two were not detected). When combining the PCR assays SP_O26_C and SP_O26_D which target two different sequences of the O26 CRISPR loci, EHEC O26:[H11] (n=77) was detected with 94.8% sensitivity (73/77 O26:[H11] were detected; the only 4 strains which are not detected were EHEC-like O26:H11 strains)

The PCR assays developed in this study for targeting the CRISPR loci of EHEC associated with the world's most frequent clinical cases were also highly specific. These assays had 97.1% to 100% specificity when tested on a very large panel of E. coli strains, giving only very minor cross-reactions (Table IV).

EXAMPLE 2: IDENTIFICATION OF GENETIC MARKERS FOR IDENTIFYING SHIGA TOXIN-PRODUCING ESCHERICHIA COLI (STEC) ASSOCIATED WITH HIGH VIRULENCE FOR HUMANS

The extended repertoire of non-LEE-encoded type III effectors (Tobe et al., 2006; Creuzburg et al., 2011) and adhesins (Spears et al., 2006; Cergole-Novella et al., 2007;) represents a most probable source of STEC virulence determinants. However, the genetic targets which support best a molecular risk assessment approach have still to be defined. Monitoring EHEC in foods requires, in particular, selection of genetic markers able to discriminate clearly EHEC from EPEC strains.

In an attempt to identify such factors, we explored the suitability of certain nle genes derived from the genomic O-islands OI-43, OI-44, OI-50, OI-57 and OI-71 as candidates to distinguish STEC strains constituting a severe risk for human health from EPEC and STEC strains that are not associated with severe and epidemic disease. E. coli gene targets used for the real-time PCR amplification are reported in Table V below.

TABLE V

| Gene (ORF name if chromosomal)[a] | Encoded protein or family effector | Genetic support (mobile elements)[a] |
|---|---|---|
| ureD (Z1142, Z1581) | Urease-associated protein UreD | OI-43 & OI-48 |
| Z1151 | Hypothetical protein | OI-43 |
| Z1153 | Hypothetical protein | OI-43 |
| Z1154 | Colicin immunity protein | OI-43 |
| Z1155 | Putative membrane protein | OI-43 |
| Z1156 | Hypothetical protein | OI-43 |
| espV (Z1387) | AvrA family effector | OI-44 |
| espK (Z1829) | Leucine-rich repeats | OI-50 |
| Z2098 | Hypothetical protein | OI-57 |
| Z6065 | Hypothetical protein | OI-71 |

[a]Nomenclature of ORFs and mobile elements refers to sequence of E. coli O157:H7 EDL933 (GenBank AE005174)

1) Genetic Markers espK, Z1151, Z1153, Z1154, Z1155, Z1156 and Z6065.

The distribution of genetic markers derived from the OI-43 (Z1151, Z1153, Z1154, Z1155, Z1156), OI-50 (espK) and OI-71 (Z6065) was examined among various E. coli pathogroups to assess their association with STEC strains with high virulence for humans.

Materials and Methods

The 1252 E. coli strains investigated in this study were divided into enterohaemorrhagic E. coli or EHEC (n=466), enteropathogenic E. coli or EPEC (n=468), Shiga-toxin producing *E. coli* or STEC (n=179) and apathogenic *E. coli* (n=139), based on the presence of stx- and eae-genes. STEC strains harbored stx only. EPEC strains harbored eae only. Apathogenic *E. coli* (n=139) were defined as stx- and eae-negative strains.

High throughput real-time PCR testing was performed as described in Example 1 above.

Primers and probes used for PCR amplifications of the genetic markers espK, Z1151, Z1153, Z1154, Z1155, Z1156 and Z6065 are listed in Table VI. Primers and probes for the detection of stx1, stx2 and eae, were described previously (Bugarel et al. 2010). Amplification of the genes stx1, stx2 and eae were used as internal controls and for group assignment purposes.

TABLE VI

|  | Forward primer, reverse primer and probe sequences (5'-3') | SEQ ID NO: |
|---|---|---|
| espK (1829) | GCAGRCATCAAAAGCGAAATCACACC | 42 |
|  | TCGTTTGGTAACTGTGGCAGATACTC | 43 |
|  | [6FAM]-ATTCAGATAGAAGAAGCGC GGGCCAG-[BHQ1] | 64 |
| Z1153 | CGATCATTGTGGGCATGTTATGCC | 50 |
|  | CCTGAATTCACACGGTGATGCG | 51 |
|  | [6FAM]-IGTAACACCCAGACGGTCA GCAACATG-[BHQ1] | 68 |
| Z1154 | GCCTTTTTATGTTCATTATTGCGGTTG | 52 |
|  | GTATAGTTTTAGCAATACCTTCCTGC | 53 |
|  | [6FAM]-TCACTTCCAGTTTCTGGTGA TGTTTTGAT-[BHQ1] | 69 |
| Z1155 | GATTGTGGCGATTAATGGGGG | 54 |
|  | ACACCGATCTGGTCATTGGCG | 55 |
|  | [6FAM]-TGGGTGAGGITAAAATAT AAAGAACGATTGC-[BHQ1] | 70 |
| Z1156 | AAACGCCTTTAAAATCTGCGTCT | 56 |
|  | TGCCGTGCGCACAGTCATAAG | 57 |
|  | [6FAM]-TAAGATATTTTCTGACT TTCCGCATGCGCTT-[BHQ1] | 71 |
| Z1151 | GCCCATGGCTCCACATCCTG | 58 |
|  | CCAAAAAGTTATGATGATTGCACTG | 59 |
|  | [6FAM]-AAAGAGCCAGCGCAGA GCTGACCAG-[BHQ1] | 72 |
| Z6065 | GCACTGGCCCTTGTTGCTCAGGC | 60 |
|  | GCTCTTCCAGTGAGAATGTCTTTCCGG | 61 |
|  | [6FAM]-TTCGCTGGAAGCAGAGCC CGTGC-[BHQ1] | 73 |

Results:

Distribution of espK, Z1151 Z1153, Z1154, Z1155, Z1156, and Z6065 and Combination Thereof Among *E. coli* Pathogroups The distribution of the different genetic markers espK, Z1151, Z1153, Z1154, Z1155, Z1156 and Z6065 among the different *E. coli* pathogroups is shown in Table VII below. Overall, the genetic markers investigated were mostly detected in EHEC strains with frequencies ranging from 51.9% (Z6065) to 90.8% (espK). These markers were less associated with EPEC strains with frequencies ranging from 17.7% (Z1154) to 53.8% (Z1155) and rarely detected in STEC (3.4 to 20.7%) and non-pathogenic *E. coli* (3.6 to 9.4%).

None of the genetic markers espK, Z1151, Z1153, Z1154, Z1155, Z1156, and Z6065 is, by itself, capable of reliably identifying all EHEC strains. However, when espK was combined with either genetic markers of the OI-43 (Z1151, Z1153, Z1154, Z1155 and Z1156), or OI-71 (Z6065) most of the EHEC strains were detected with frequencies ranging from 95.5% (espK/Z6065) to 98.3% (espK/Z1155). The same combinations detected EPEC strains with frequencies ranging from 31.2% (espK/Z1156) to 61.8% (espK/Z1155), STEC strains with frequencies of 6.7% to 23.5% and non-pathogenic *E. coli* strains with frequencies between 7.9% and 13.7%.

TABLE VII

| Genetic markers | EHEC (n = 466) | EPEC (n = 468) | STEC (n = 179) | EC (n = 139) |
|---|---|---|---|---|
| Z1151 | 79.8% | 20.3% | 20.7% | 7.9% |
| Z1153 | 89.3% | 23.9% | 12.3% | 9.4% |
| Z1154 | 83.3% | 17.7% | 3.4% | 3.6% |
| Z1155 | 79.4% | 53.8% | 16.8% | 8.6% |
| Z1156 | 88.8% | 18.8% | 12.8% | 6.5% |
| Z6065 | 51.9% | 20.1% | 5.0% | 8.6% |
| espK | 90.8% | 28.0% | 3.4% | 5.0% |
| espK/Z1151 | 97.2% | 34.0% | 23.5% | 12.2% |
| espK/Z1153 | 97.4% | 35.7% | 15.1% | 13.7% |
| espK/Z1154 | 97.0% | 31.8% | 6.7% | 7.9% |
| espK/Z1155 | 98.3% | 61.8% | 19.6% | 12.9% |
| espK/Z1156 | 97.4% | 31.2% | 15.6% | 10.1% |
| espK/Z6065 | 95.5% | 36.8% | 8.4% | 13.7% | espK/Z1151 represent strains giving a positive result for espK and/or Z1151;
espK/Z1153 represent strains giving a positive result for espK and/or Z1153;
espK/Z1154 represent strains giving a positive result for espK and/or Z1154;
espK/Z1155 represent strains giving a positive result for espK and/or Z1155;
espK/Z1156 represent strains giving a positive result for espK and/or Z1156;
espK/Z6065 represent strains giving a positive result for espK and/or Z6065

Distribution of the Genetic Markers in Enterohaemorrhagic *E. coli*

The distribution of each genetic marker espK, Z1151, Z1153, Z1154, Z1155, Z1156 and Z6065 was significantly different according to EHEC serotypes (Table VIII). Interestingly, the genetic marker Z6065 is the unique genetic marker able to detect EHEC O104:H4 (stx positive, eae negative, aggR positive) that has been involved in the large German outbreak in 2011.

Except Z1151 which was not detected in any EHEC O45:[H2] and Z6065 which was absent from 18 out of the tested 19 O121:[H19] (5.3%), all the other genetic markers investigated were found in EHEC strains of the top 7 serotypes, with frequencies ranging from 15.4% (prevalence of Z6065 in O26: [H11]) to 100%.

By combining espK with one of the following genetic markers of the OI-43: Z1151, Z1153, Z1154, Z1155 and Z1156, most of EHEC strains of top 7 EHEC serotypes were detected. Thus, whatever the combination of genetic markers used, all EHEC strains of the top 7 serotypes were tested positive, with the exception of 1 to 2 strains of EHEC O121:[H19] which tested negative with espK/Z1154 and espK/Z6065 respectively; one strain of O103:[H2] that failed to be detected with espK/Z1154 and 7 to 8 strains of EHEC O26:[H11] which were found negative with all tested associations of genetic markers. Hence, only few EHEC strains did not react with the genetic markers tested here. These could be aberrant strains, not representative for the classical EHEC types. Looking at other genes in these anecdotal strains or sequencing their genome might reveal more differences which make things clearer regarding their status. We should assume, in the principle, that it is not necessarily the case that all members of a particular serotype would be EHEC.

Interestingly, other EHEC strains, with other serotypes than those of the top7 serotypes, were highly detected with frequencies ranging from 87.5% to 95.5%. This finding indicated that the tested combinations of the genetic markers could detect typical EHEC (*E. coli* strains both stx and eae positive) with high sensitivity. The introduction of the genetic marker Z6065 allows detecting in addition EHEC O104:H4 (stx positive, eae negative, aggR positive) that has been involved in the large German outbreak in 2011.

but its prevalence in other *E. coli* pathogroups has not been documented yet. In this study, we evaluated the distribution of ureD, espV, espK, and Z2098 in various *E. coli* pathogroups to assess their association with STEC strains with high virulence for humans and to test their suitability for clearly distinguishing EHEC from other *E. coli* pathogroups.

TABLE VIII

| Genetic markers | O26:H11 (n = 117) | O45:H2 (n = 19) | O103:H2 (n = 61) | O111:H8 (n = 33) | O121:H19 (n = 19) | O145:H28 (n = 31) | O157:H7 (n = 98) | Other EHEC (n = 88) |
|---|---|---|---|---|---|---|---|---|
| Z1151 | 105/117 (89.7%) | 0/19 (0%) | 44/61 (72.1%) | 33/33 (100%) | 5/19 (26.3%) | 30/31 (96.8%) | 91/98 (92.9%) | 64/88 (72.7%) |
| Z1153 | 107/117 (91.5%) | 19/19 (100%) | 48/61 (78.7%) | 33/33 (100%) | 18/19 (94.7%) | 31/31 (100%) | 91/98 (92.9%) | 69/88 (78.4%) |
| Z1154 | 87/117 (74.4%) | 19/19 (100%) | 48/61 (78.7%) | 31/33 (93.9%) | 15/19 (78.9%) | 29/31 (93.5%) | 91/98 (92.9%) | 68/88 (77.3%) |
| Z1155 | 75/117 64.1% | 16/19 (84.2%) | 41/61 (67.2%) | 33/33 (100%) | 14/19 (73.7%) | 25/31 (80.6%) | 97/98 (99.0%) | 69/88 (78.4%) |
| Z1156 | 106/117 (90.6%) | 19/19 (100%) | 48/61 (78.7%) | 33/33 (100%) | 18/19 (94.7%) | 31/31 (100%) | 91/98 (92.9%) | 68/88 (77.3%) |
| Z6065 | 18/117 (15.4%) | 19/19 (100%) | 59/61 (96.7%) | 7/33 (21.2%) | 1/19 (5.3%) | 6/31 (19.4%) | 85/98 (86.7%) | 47/88 (53.4%) |
| espK | 108/117 (92.3%) | 19/19 (100%) | 60/61 (98.4%) | 33/33 (100%) | 17/19 (89.5%) | 31/31 (100%) | 92/98 (93.9%) | 63/88 (71.6%) |
| espK/Z1151 | 110/117 (94.0%) | 19/19 (100%) | 61/61 (100%) | 33/33 (100%) | 19/19 (100%) | 31/31 (100%) | 98/98 (100%) | 82/88 (93.2%) |
| espK/Z1153 | 110/117 (94.0%) | 19/19 (100%) | 61/61 (100%) | 33/33 (100%) | 19/19 (100%) | 31/31 (100%) | 98/98 (100%) | 83/88 (94.3%) |
| espK/Z1154 | 110/117 (94.0%) | 19/19 (100%) | 60/61 (98.4%) | 33/33 (100%) | 18/19 (94.7%) | 31/31 (100%) | 98/98 (100%) | 83/88 (94.3%) |
| espK/Z1155 | 113/117 (96.6%) | 19/19 (100%) | 61/61 (100%) | 33/33 (100%) | 19/19 (100%) | 31/31 (100%) | 98/98 (100%) | 84/88 (95.5%) |
| espK/Z1156 | 110/117 (94.0%) | 19/19 (100%) | 61/61 (100%) | 33/33 (100%) | 19/19 (100%) | 31/31 (100%) | 98/98 (100%) | 83/88 (94.3%) |
| espK/Z6065 | 109/117 (93.2%) | 19/19 (100%) | 61/61 (100%) | 33/33 (100%) | 17/19 (89.5%) | 31/31 (100%) | 98/98 (100%) | 77/88 (87.5%) | espK/Z1151 represent strains giving a positive result for espK and/or Z1151; espK/Z1153 represent strains giving a positive result for espK and/or Z1153; espK/Z1154 represent strains giving a positive result for espK and/or Z1154; espK/Z1155 represent strains giving a positive result for espK and/or Z1155; espK/Z1156 represent strains giving a positive result for espK and/or Z1156; espK/Z6065 represent strains giving a positive result for espK and/or Z6065

2) Genetic Markers espK, espV, Z2098 and UreD

The production of Shiga toxin (Stx) by enterohemorrhagic *E. coli* (EHEC) is the primary virulence trait responsible for Hemorrhagic colitis (HC) and Hemolytic Uremic Syndrome (HUS), but many *E. coli* strains that produce Stx (STEC) do not cause HC and HUS. Besides the ability to produce one or more types of Shiga toxins, STEC strains associated with human infections harbor other factors which might be used to distinguish STEC strains constituting a severe risk for human health from STEC strains that are not associated with severe and epidemic disease. In an attempt to identify such factors, we explored the suitability of certain nle genes derived from the genomic O-island OI-43, OI-44, OI-50, and OI-57 as candidates to distinguish STEC strains constituting a severe risk for human health from EPEC and STEC strains that are not associated with severe and epidemic disease. We focused on ureD (urease activity) encoded by OI-43 and/or OI-48, espK (EspK) carried by OI-50, a locus involved in persistence of EHEC O157:H7 in the intestines of orally inoculated calves (Vlisidou et al. 2006). Also, we focused on Z2098, a sequence derived from OI-57, a genomic island that may be associated with increased virulence of STEC strains to humans (Coombes et al., 2008; Imamovic et al, 2010; Bugarel et al., 2011). Genome sequencing of EHEC strains (EHEC O157:H7, O111, O103 and O26) has also pointed out other genetic markers, such as espV whose role in disease has not been evaluated. This gene is located on OI-44 of EHEC O157:H7

Materials and Methods

*E. coli* strains (n=1100) used in this study were mainly those described in the above studies. The EHEC type strains (n=340) and were defined on the presence of stx- and eae-genes. STEC strains (n=193) harbored stx only. EPEC strains (n=392) harbored eae only. Apathogenic *E. coli* (n=175) were defined as stx- and eae-negative strains. Cultivation of bacteria and preparation of DNA was performed as previously described.

High-throughput real-time PCR amplifications were also performed as described above.

Primers and FAM-labeled TaqMan® probes used for PCR amplifications of stx1, stx2, and eae were previously described (Bugarel al. 2010). Primers and probes used for targeting ureD, espK, Z2098 and espV are listed in Table IX below.

TABLE IX

| Target gene[a] | Forward primer, reverse primer and probe sequences (5'-3') | SEQ ID NO: | Location within sequence AE005174 |
|---|---|---|---|
| espK (Z1829) | GCAGRCATCAAAAGCGAAATCACACC | 42 | 1673422-1673397 |
| | TCGTTTGGTAACTGTGGCAGATACTC | 43 | 1673312-1673338 |
| | [6FAM]-ATTCAGATAGAAGAAGC GCGGGCCAG-[BHQ] | 64 | 1673395-16673370 |

TABLE IX-continued

| Target gene[a] | Forward primer, reverse primer and probe sequences (5'-3') | SEQ ID NO: | Location within sequence AE005174 |
|---|---|---|---|
| espV (Z1387) | TCAGGTTCCTCGTCTGATGCCGC | 44 | 1295446-1295424 |
| | CTGGTTCAGGCCTGGAGCAGTCC | 45 | 1295360-1295382 |
| | [6FAM]-CTTGCAACACGTTACGC TGCCGAGTATT-[BHQ] | 65 | 1295422-1295395 |
| ureD (Z1142) | GCAATAATTGACTCTGATTGCC | 46 | 1078824-1078845 |
| | GCTGCTGCGGTAAAATTTACT | 47 | 1078892-1078872 |
| | [6FAM]-TACGCTGATCACCAT GCCTGGTGC-[BHQ] | 66 | 1078847-1078870 |
| Z2098 | CTGAAAAGAGCCAGAACGTGC | 48 | 1888173-1888193 |
| | TGCCTAAGATCATTACCCGGAC | 49 | 1888308-1888287 |
| | [HEX]TAACTGCTATACCTC CGCGCCG[BHQ] | 67 | 1888286-1888265 |

[a]Numbering as in EDL933

Results
Distribution of ureD espV, espK, and Z2098 and Combination Thereof Among *E. coli* Pathogroups Distribution of the genetic markers ureD, espV, espK, and Z2098 among the different *E. coli* pathogroups is shown in Table X. Overall, the genetic markers investigated were mostly detected in EHEC strains with frequencies ranging from 84.4% (espV) to 92.4% (espK). These markers were less associated with EPEC strains with frequencies ranging from 18.1% (ureD) to 45.2% (espV) and rarely detected in STEC (0.5 to 3.6%) and non-pathogenic *E. coli* (0.6 to 2.9%). Overall, we observed that 26.5% of the EPEC strains which tested positive for at least one of the investigated genetic markers belonged to the top7 EHEC serotypes. Thus, it is noteworthy that 57/113 EPEC strains that are positive for espK belonged to the top7 EHEC serotypes. Likewise 59/177 EPEC strains positive for espy belonged to the top7 EHEC serotypes. It is also remarkable that 68/91 EPEC positive for Z2098 and 58/71 EPEC strains positive for ureD belonged to the top7 EHEC serotypes as well. Interestingly, other EPEC strains having a known EHEC serotype such as O55:H7, O103:H25 and O156:H25 were also found positive for at least one of these genetic markers (data not shown). These findings would indicate that such isolates might be Stx-negative derivatives of EHEC that are also designated as EHEC-like strains (Bugarel et al. 2011). We assumed these isolates were EHEC-derivatives according to their serotypes and nle genes content but they might also be EPEC strains that we are unable to discriminate from EHEC derivatives yet. Further investigation using whole genome sequencing may clarify the exact designation of these strains in the future.

None of the genetic markers ureD, espV, espK, and Z2098 is, by itself, capable of reliably identifying all EHEC strains. Combinations of the genetic markers were explored to identify those which detect EHEC with best specificity. The results are presented in Table X. In combination those genetic markers were highly associated with EHEC with frequencies ranging from 97.9% (espK/Z2098) to 98.8% (espK/ureD). The same combinations detected EPEC strains with frequencies ranging from 33.4% (espK/ureD) to 54.1% (espK/espV), STEC strains with frequencies of 1.6% to 3.6% and non-pathogenic *E. coli* strains with frequencies between 1.1% and 3.4%.

TABLE X

| Genetic markers | EHEC (n = 340) | EPEC (n = 392) | STEC (n = 193) | EC (n = 175) |
|---|---|---|---|---|
| espK | 92.4% | 28.8% | 0.5% | 1.1% |
| ureD | 89.4% | 18.1% | 3.1% | 2.9% |
| Z2098 | 87.4% | 23.2% | 3.6% | 1.1% |
| espV | 84.4% | 45.2% | 1.6% | 0.6% |
| espK/espV | 98.5% | 54.1% | 1.6% | 1.1% |
| espK/ureD | 98.8% | 33.4% | 3.6% | 3.4% |
| espK/Z2098 | 97.9% | 36.7% | 3.6% | 2.3% | espK/espV represent strains giving a positive result for espK and/or espV;
espK/ureD represent strains giving a positive result for espK and/or ureD;
espK/Z2098 represent strains giving a positive result for Z2098 and/or espK Distribution of ureD, espV, espK, espN, Z2098 and espM1 and Combination Thereof Among EHEC Serotypes The distribution of each genetic marker ureD, espV, espK, and Z2098 was significantly different according to EHEC serotypes. Distribution of each genetic marker in various EHEC serogroups is reported in Table XI. Except espV which was not detected in any EHEC O45:[H2], all the other genetic markers investigated were found highly prevalent in EHEC strains of the top 7 serotypes, with frequencies ranging from 71.4% (prevalence of ureD in O103:[H2]) to 100%.

TABLE XI

| Genetic markers | Top7 EHEC serotypes | O103:H2 | O111:H8 | O121:H19 | O145:H28 | O157:H7 | O26:H11 | O45:H2 | Other EHEC (new emerging EHEC)[a] | Total EHEC |
|---|---|---|---|---|---|---|---|---|---|---|
| Z2098 | 250/277 (90.3%) | 49/49 (100%) | 47/51 (92.2%) | 17/20 (85.00%) | 30/30 (100%) | 49/66 (74.2%) | 44/44 (100%) | 14/17 (82.4%) | 47/63 (74.6%) | 297/340 (87.4%) |
| espK | 269/277 (97.1%) | 48/49 (98.0%) | 51/51 (100%) | 19/20 (95.0%) | 29/30 (96.7%) | 61/66 (92.4%) | 43/44 (97.7%) | 17/17 (100%) | 45/63 (71.4%) | 314/340 (92.4%) |
| espV | 248/277 (89.5%) | 48/49 (98.0%) | 51/51 (100%) | 20/20 (100%) | 30/30 (100%) | 65/66 (98.5%) | 34/44 (77.3%) | 0/17 (0%) | 39/63 (61.9%) | 287/340 (84.4%) |
| ureD | 257/277 (92.8%) | 35/49 (71.4%) | 51/51 (100%) | 16/20 (80.0%) | 30/30 (100%) | 64/66 (97.0%) | 44/44 (100%) | 17/17 (100%) | 47/63 (74.6%) | 304/340 (89.4%) |

[a]O103:[H25] (n = 2), O118:[H16] (n = 4), O118:H2, O119:[H25] (n = 5), O123:H11, O127:H8s, O145, O145:[H25] (n = 5), O156:H21, O156:H25 (n = 11), O165:H25 (n = 2), O172:[H25] (n = 2), O172:NM, O177 (n = 2), O177:[H25], O182:[H25], O3, O49:H16, O5 (n = 11), O55:[H7] (n = 2), O76:H51, O84:H2, Ont:[H2], Ont:H25 (n = 2), Or:H16, OX186:[H2].

Detection of the top 7 EHEC serotypes based on different combinations of these genetic markers is reported in Table XII. Detection of espK and/or Z2098 allowed detecting most of the EHEC serotypes associated with human infections. Thus, all EHEC O111:[H8], O26:[H11], O45:[H2], O103:[H2] and O145:[H28] strains gave a positive result for espK and/or Z2098, while 97.0% of O157:[H7] and 95% of O121:[H19] were tested positive. The association of espK with either espV or ureD allowed detecting most of the strains of the top 7 EHEC serotypes as well. Hence, all strains of serotypes O157:[H7], O145:[H28], O111:[H8], O103:[H2], O45:[H2] and O121:[H19] gave a positive results for espK and/or espV, and 97.7% of O26:[H11] gave a positive result for espK and/or espV. Data were very similar when testing espK in association with ureD. In that case, all strains of the top7 EHEC serotypes gave a positive result for espK and/or ureD.

espK and/or espV. Most STEC and a virulent E. coli strains were found negative with both espK and espV. Another interesting approach was to associate espK with Z2098. This combination of genetic markers resulted in the detection of 99.3% of EHEC strains belonging to the seven major EHEC serotypes and in 93.7% of EHEC strains with serotypes other than those of the top7 serotypes. Detection of espK and/or Z2098 was reported for only 36.7% of EPEC, 3.6% of STEC and 2.3% of apathogenic E. coli strains. The best approach for detecting EHEC with the highest specificity and sensitivity was to combine espK with ureD. This association allowed detecting 100% of EHEC of the top 7 serotypes and 93.7% of EHEC strains with other serotypes.

TABLE XII

| Gene association | Top7 EHEC serotypes | O103:H2 | O111:H8 | O121:H19 | O145:H28 | O157:H7 | O26:H11 | O45:H2 | Other EHEC (new emerging EHEC)[a] | Total EHEC |
|---|---|---|---|---|---|---|---|---|---|---|
| espK/espV | 276/277 (99.6%) | 49/49 (100%) | 51/51 (100%) | 20/20 (100%) | 30/30 (100%) | 66/66 (100%) | 43/44 (97.7%) | 17/17 (100%) | 59/63 (93.7%) | 335/340 (98.5%) |
| espK/ureD | 277/277 (100%) | 49/49 (100%) | 51/51 (100%) | 20/20 (100%) | 30/30 (100%) | 66/66 (100%) | 44/44 (100%) | 17/17 (100%) | 59/63 (93.7%) | 336/340 (98.8%) |
| espK/Z2098 | 275/277 (99.3%) | 49/49 (100%) | 51/51 (100%) | 19/20 (95.0%) | 30/30 (100%) | 65/66 (98.5%) | 44/44 (100%) | 17/17 (100%) | 59/63 (93.7%) | 334/340 (98.2%) |

[a]O103:[H25] (n = 2), O118:[H16] (n = 4), O118:H2, O119:[H25] (n = 5), O123:H11, O127:H8s, O145, O145:[H25] (n = 5), O156:H21, O156:H25 (n = 11), O165:H25 (n = 2), O172:[H25] (n = 2), O172:NM, O177 (n = 2), O177:[H25], O182:[H25], O3, O49:H16, O5 (n = 11), O55:[H7] (n = 2), O76:H51, O84:H2, Ont:[H2], Ont:H25 (n = 2), Or:H16, OX186:[H2].
espK/espV represent strains giving a positive result for espK and/or espV; espK/ureD represent strains giving a positive result for espK and/or ureD; espK/Z2098 represent strains giving a positive result for Z2098 and/or espK 3) Summary:

The above studies allowed selecting genetic markers Z1151, Z1153, Z1154, Z1155, Z1156, Z6065, ureD, espV, espK and Z2098 useful for detecting typical EHEC strains and in particular those belonging to the seven major serotypes of EHEC reported worldwide in human infections. The distribution of these different genetic markers has been investigated among the different E. coli pathogroups, allowing designing optimal sub-combinations of these markers. The results of these studies are summarized below.

The genetic markers ureD, espV, espK, Z2098, Z1151, Z1153, Z1154, Z1155, Z1156 and Z6065 were detected at different frequencies among the EHEC serotypes. We explored the various associations of these genetic markers to search for the best combinations of markers giving the higher specificity and sensitivity for detecting EHEC. Association of the genetic marker espK with one of the other nine genetic markers allows detecting most of the typical EHEC strains and in particular those belonging to the top7 EHEC serotypes. The genetic markers espV, ureD and Z2098 were shown the best candidates to be combined with espK for detecting EHEC. Taken individually they were not able to detect all strains of the top 7 EHEC serotypes, while in association they detected 99.3% to 100% of the top 7 EHEC strains. The association of espK with either espV, ureD or Z2098 proved to be the best combinations for a more specific and sensitive detection of EHEC strains. Hence, a positive result for espK and/or espV was observed in 99.6% of EHEC strains belonging to the seven major serotypes of EHEC reported worldwide in human infections (only one EHEC O26:H11 isolate tested negative). Also, 93.7% of EHEC strains with serotypes other than those of the top 7 serotypes were tested positive for espK and/or espV. In final, only a subset (54.1%) of EPEC strains tested positive for espK and/or espV. Detection of espK and/or ureD was also reported for only 33.4% of EPEC, 3.6% of STEC and 3.4% of apathogenic E. coli strains.

These findings showed that combining detection of espK with either espV, ureD or Z2098 is a highly sensitive and specific approach for identifying with ≥99% confidence EHEC serotypes related to the world's most frequent clinical cases. Detection of these genetic markers in combination with stx in complex samples (food or fecal specimens) would provide a more EHEC-targeted diagnostic than that combining only stx and eae. Interestingly, introduction of Z6065 in the detection scheme allow detecting the atypical EHEC O104:H4 that was involved in the severe and largest STEC outbreak that occurred in Europe. Given the rapidity of these PCR assays, this approach should have a major impact on top7 EHEC surveillance and outbreak investigations and is likely to be of benefit to public health. Moreover, detection of these sets of genetic markers in 93.7% of EHEC strains having serotypes other than those of the top7 EHEC serotypes may be helpful to identify new emerging EHEC strains.

CONCLUSION

We used a high throughput PCR approach to explore the virulome of different E. coli pathogroups in an attempt to identify genetic traits that would characterize pathogenic STEC strains. The distribution of ten genetic markers (Z1151, Z1153, Z1154, Z1155, Z1156, Z6065, ureD, espV, espK and Z2098) was investigated in a large panel of E. coli comprising EHEC, EPEC, STEC and apathogenic E. coli strains. The distribution of these genetic markers varied between the E. coli pathogroups and according to the serotypes.

Overall, the associations of espK with the other nine genes (Z1151, Z1153, Z1154, Z1155, Z1156, Z6065, ureD, espV, and Z2098) were shown the best combinations for detecting EHEC strains belonging to the seven major serotypes of EHEC reported worldwide in human infections. These findings showed that using this relevant combinations of genes most of the EHEC strains were tested positive while only a subset of the EPEC strains were cross reacting. Also, only very minor STEC and a virulent *E. coli* strains cross-reacted when using such an approach. In addition to the detection of typical EHEC strains the combination espK/Z6065 allows detecting the atypical EHEC O104:H4 (stx positive, eae negative, aggR positive) that was involved in the larger epidemy of HC and HUS that occurred in Europe in 2011.

REFERENCES

Beutin, L., S. Jahn, and P. Fach. 2009. Evaluation of the 'GeneDisc' real-time PCR system for detection of enterohaemorrhagic *Escherichia coli* (EHEC) O26, O103, O111, O145 and O157 strains according to their virulence markers and their O- and H-antigen-associated genes. J. Appl. Microbiol. 106(4): 1122-1132.

Bugarel M, Martin A, Fach P, Beutin L. 2011. Virulence gene profiling of enterohemorrhagic (EHEC) and enteropathogenic (EPEC) *Escherichia coli* strains: a basis for molecular risk assessment of typical and atypical EPEC strains. BMC Microbiol. June 21; 11:142.

Bugarel M, Beutin L, Scheutz F, Loukiadis E, Fach P. 2011. Identification of genetic markers for differentiation of Shiga toxin-producing, enteropathogenic, and avirulent strains of *Escherichia coli* O26. Appl Environ Microbiol. April; 77(7):2275-81.

Bugarel M, Beutin L, Martin A, Gill A, Fach P. 2010. Micro-array for the identification of Shiga toxin-producing *Escherichia coli* (STEC) seropathotypes associated with Hemorrhagic Colitis and Hemolytic Uremic Syndrome in humans. Int J Food Microbiol. September 1; 142(3):318-29.

Bugarel M, Beutin L, Fach P. 2010. Low-density macroarray targeting non-locus of enterocyte effacement effectors (nle genes) and major virulence factors of Shiga toxin-producing *Escherichia coli* (STEC): a new approach for molecular risk assessment of STEC isolates. Appl Environ Microbiol. January; 76(1):203-11.

Cergole-Novella M C, Nishimura L S, Dos Santos L F, Irino K, Vaz T M, Bergamini A M, Guth B E. 2007. Distribution of virulence profiles related to new toxins and putative adhesins in Shiga toxin-producing *Escherichia coli* isolated from diverse sources in Brazil. FEMS Microbiol Lett. September; 274(2):329-34. Epub 2007 July 25.

Chang, C. 1991 "Branched DNA Amplification Multimers for the Sensitive, Direct Detection of Human Hepatitis Viruses," Nucleic Acids Symposium Series, no. 24: 197-200.

Compton, J. 1991 "Nucleic Acid Sequence-Based Amplification," Nature 350, no. 6313: 91-92.

Coombes B K, Wickham M E, Mascarenhas M, Gruenheid S, Finlay B B, Karmali M A. 2008. Molecular analysis as an aid to assess the public health risk of non-O157 Shiga toxin-producing *Escherichia coli* strains. Appl Environ Microbiol. April; 74(7):2153-60.

Creuzburg K, Middendorf B, Mellmann A, Martaler T, Holz C, Fruth A, Karch H, Schmidt H. 2011. Evolutionary analysis and distribution of type III effector genes in pathogenic *Escherichia coli* from human, animal and food sources. Environ Microbiol. February; 13(2):439-52.

Frank C, Werber D, Cramer J P, Askar M, Faber M, an der Heiden M, Bernard H, Fruth A, Prager R, Spode A, Wadl M, Zoufaly A, Jordan S, Kemper M J, Follin P, Müller L, King L A, Rosner B, Buchholz U, Stark K, Krause G; HUS Investigation Team. Epidemic profile of Shiga-toxin-producing *Escherichia coli* O104:H4 outbreak in Germany. N Engi J Med. 2011 November 10; 365(19): 1771-80

Gault G, Weill F X, Mariani-Kurkdjian P, Jourdan-da Silva N, King L, Aldabe B, Charron M, Ong N, Castor C, Mace M, Bingen E, Noel H, Vaillant V, Bone A, Vendrely B, Delmas Y, Combe C, Bercion R, d'Andigne E, Desjardin M, de Valk H, Rolland P. Outbreak of haemolytic uraemic syndrome and bloody diarrhoea due to *Escherichia coli* O104:H4, south-west France, June 2011. Euro Surveill. 2011 June 30; 16(26).

Imamovic L, Tozzoli R, Michelacci V, Minelli F, Marziano M L, Caprioli A, Morabito S. 2010. OI-57, a genomic island of *Escherichia coli* O157, is present in other seropathotypes of Shiga toxin-producing *E. coli* associated with severe human disease. Infect Immun. November; 78(11):4697-704.

Katinali, M. A., M. Mascarenhas, S. Shen, K. Ziebell, S. Johnson, R. Reid-Smith, J. Isaac-Renton, C. Clark, K. Rahn, and J. B. Kaper. 2003. Association of genomic O island 122 of *Escherichia coli* EDL 933 with verocyto-toxin-producing *Escherichia coli* seropathotypes that are linked to epidemic and/or serious disease. J. Clin. Microbiol. 41: 4930-4940.

Levine, M. M. 1987. *Escherichia coli* That Cause Diarrhea—Enterotoxigenic, Enteropathogenic, Enteroinvasive, Enterohemorrhagic, and Enteroadherent. J. Infect. Dis. 155: 377-389.

Mackay, I. 2007. Real-time PCR in Microbiology, from diagnosis to characterization. Caister Academic Press, Norfolk, U K.

Nataro, J. P. and J. B. Kaper. 1998. Diarrheagenic *Escherichia coli*. Clinical Microbiol. Rev. 11: 142-201.

Notomi, T., Okayama, H., Masubuchi, H., Yonekawa, T., Watanabe, K., Amino, N., and Hase, T. 2000 Loop-Mediated Isothermal Amplification of DNA. Nucleic Acids Research 28, no. 12: E63.

Scheutz F, Nielsen E M, Frimodt-Møller J, Boisen N, Morabito S, Tozzoli R, Nataro J P, Caprioli A. Characteristics of the enteroaggregative Shiga toxin/verotoxin-producing *Escherichia coli* O104:H4 strain causing the outbreak of haemolytic uraemic syndrome in Germany, May to June 2011. Euro Surveill. 2011 June 16; 16(24).

Spears K J, Roe A J, Gaily D L. 2006. A comparison of enteropathogenic and enterohaemorrhagic *Escherichia coli* pathogenesis. FEMS Microbiol Lett. February; 255 (2):187-202.

Struelens M J, Palm D, Takkinen J. Enteroaggregative, Shiga toxin-producing *Escherichia coli* O104:H4 outbreak: new microbiological findings boost coordinated investigations by European public health laboratories. Euro Surveill. 2011 June 16; 16(24).

Tobe T, Beatson S A, Taniguchi H, Abe H, Bailey C M, Fivian A, Younis R, Matthews S, Marches O, Frankel G, Hayashi T, Pallen M J. 2006. An extensive repertoire of type III secretion effectors in *Escherichia coli* O157 and the role of lambdoid phages in their dissemination. Proc Natl Acad Sci USA. October 3; 103(40):14941-6.

Vlisidou I, Marchés O, Dziva F, Mundy R, Frankel G, Stevens M P. 2006. Identification and characterization of EspK, a type III secreted effector protein of enterohaemorrhagic *Escherichia coli* O157:H7. FEMS Microbiol Lett. October; 263(1):32-40.

Walker, G., Fraiser, M., Schram, J., Little, M., Nadeau, J., and Douglas P. Malinowski, D. 1992 Strand Displacement Amplification—An Isothermal, In Vitro DNA Amplification Technique, Nucleic Acids Research 20, no. 7: 1691-1696.

The invention claimed is:

1. A method for detecting serotype(s) of enterohemorrhagic *Escherichia coli* (EHEC) suspected to be present in a food product, wherein said method comprises detecting the presence or the absence, in said food product or DNA isolated therefrom, of at least one of the following *E. coli* Clustered Regularly Interspaced Short Palindromic Repeats (CRISPR) sequences:
   a) CRISPR sequences for detecting EHEC O157:[H7] wherein said CRISPR sequences are selected among
      the CRISPR sequences SEQ ID NO: 1, SEQ ID NO: 2, and SEQ ID NO: 3, wherein the presence of one or more of said CRISPR SEQ ID NO: 1-3 is indicative of the presence of EHEC O157:[H7]; and/or
      the CRISPR sequence SEQ ID NO: 4, wherein the presence of said CRISPR sequence is indicative of the presence of EHEC O157:[H7];
   b) a CRISPR sequence for detecting EHEC O145:[H28], wherein said CRISPR sequence is the sequence SEQ ID NO: 5, and wherein the presence of said CRISPR sequence is indicative of the presence of EHEC O145:[H28]; and
   c) a CRISPR sequence for detecting EHEC O111:[H8], wherein said CRISPR sequence is the sequence SEQ ID NO: 6, and wherein the presence of said CRISPR sequence is indicative of the presence of EHEC O111:[H8]; and
   d) a CRISPR sequence for detecting EHEC O121:[H19], wherein said CRISPR sequence is the sequence SEQ ID NO: 7, and wherein the presence of said CRISPR sequence is indicative of the presence of EHEC O121:[H19]; and
   e) a CRISPR sequence for detecting EHEC O103:[H2] and/or EHEC O45:[H2], wherein said CRISPR sequence is the sequence SEQ ID NO: 8, and wherein the presence of said CRISPR sequence is indicative of the presence of EHEC O103:[H2] and/or of EHEC O45:[H2]; and
   f) a CRISPR sequence for detecting EHEC O104:[H4], wherein said CRISPR sequence is the sequence SEQ ID NO: 9, and wherein the presence of said CRISPR sequence is indicative of the presence of EHEC O104:[H4]; and
   g) a CRISPR sequence for detecting EHEC O26:[H11], wherein said CRISPR sequence is the sequence SEQ ID NO: 10, and wherein the presence of said CRISPR sequence is indicative of the presence of EHEC O26:[H11].

2. The method of claim 1, wherein said method comprises performing a PCR assay on said food product or DNA isolated therefrom with a combination of primers targeting said CRISPR sequences.

3. The method of claim 2, wherein said combination of primers comprises:
   a) primers for detecting EHEC O157:[H7], wherein said primers consist of:
      a set of primers targeting both the CRISPR sequences SEQ ID NO: 1 and SEQ ID NO: 2, wherein said primers are defined by the following sequences:

SEQ ID NO: 11 and
SEQ ID NO: 12,
a set of primers targeting the CRISPR sequence SEQ ID NO: 3 wherein said primers are defined by the following sequences:
SEQ ID NO: 13 and
SEQ ID NO: 14,
wherein the presence of an amplification product for at least one of said sets of primers is indicative of the presence of EHEC O157:[H7]; and/or:
a set of primers targeting the CRISPR sequence SEQ ID NO: 4, wherein said primers are defined by the following sequences:
SEQ ID NO: 15 and
SEQ ID NO: 16,
wherein the presence of an amplification product for said set of primers is indicative of the presence of EHEC O157:[H7]; and
b) primers for detecting EHEC O145:[H28], wherein said primers consist of:
a set of primers targeting the CRISPR sequence SEQ ID NO: 5, wherein said primers are defined by the following sequences:
SEQ ID NO: 17 and
SEQ ID NO: 18,
wherein the presence of an amplification product for said set of primers is indicative of the presence of EHEC O145:[H28]; and
c) primers for detecting EHEC O111:[H8], wherein said primers consist of:
a set of primers targeting the CRISPR sequence SEQ ID NO: 6, wherein said primers are defined by the following sequences:
SEQ ID NO: 19,
SEQ ID NO: 20, and
SEQ ID NO: 21,
wherein the presence of an amplification product for at least one of primers pairs SEQ ID NO: 19 and SEQ ID NO: 20 or SEQ ID NO: 19 and SEQ ID NO: 21 is indicative of the presence of EHEC O111:[H8]; and
d) primers for detecting EHEC O121:[H19], wherein said primers consist of:
a set of primers targeting the CRISPR sequence SEQ ID NO: 7, wherein said primers are defined by the following sequences:
SEQ ID NO: 22 and
SEQ ID NO: 23,
wherein the presence of an amplification product for said set of primers is indicative of the presence of EHEC O121:[H19]; and
e) primers for detecting EHEC O103:[H2] and/or EHEC O45:[H2], wherein said primers consist of:
a set of primers targeting the CRISPR sequence SEQ ID NO: 8, wherein said primers are defined by the following sequences:
SEQ ID NO: 24 and
SEQ ID NO: 25,
wherein the presence of an amplification product for said set of primers is indicative of the presence of EHEC O103:[H2] and/or of EHEC O45:[H2]; and
f) primers for detecting EHEC O104:[H4], wherein said primers consist of:
a set of primers targeting the CRISPR sequence SEQ ID NO: 9, wherein said primers are defined by the following sequences:
SEQ ID NO: 26 and
SEQ ID NO: 27;
wherein the presence of an amplification product for said set of primers is indicative of the presence of EHEC O104:[H4]; and
g) primers for detecting EHEC O26:[H11], wherein said primers consist of:
two sets of primers targeting the CRISPR sequence SEQ ID NO: 10, wherein the first primers set is defined by the following sequences:
SEQ ID NO: 28 and
SEQ ID NO: 29
and the second said primers set is defined by the following sequences:
SEQ ID NO: 30 and
SEQ ID NO: 31;
wherein the presence of an amplification product for at least one of the said sets of primers is indicative of the presence of EHEC O26:[H11].

4. A method for detecting whether a food product contains EHEC of at least one of EHEC O157:[H7], O145:[H28], O103:[H2], O111:[H8], O121:[H19], O26:[H11], O45:[H2] and O104:[H4] serotypes, wherein said method comprises the detection of the espK gene, the detection of the Z6065 gene, and the detection of at least one gene selected from the group consisting of espV, ureD, Z2098, Z1151, Z1153, Z1154, Z1155, and Z1156.

5. The method of claim 4, wherein said method comprises performing a PCR assay on said food product or DNA isolated therefrom with a combination of primers comprising a set of primers derived from espK, a set of primers derived from Z6065, and a set of primers derived from at least one of espy, ureD, Z2098, Z1151, Z1153, Z1154, Z1155, and Z1156, and detecting the presence or the absence of an amplification product for each set of primers of said combination.

6. The method of claim 4, which further comprises performing a PCR assay on said food product sample or DNA isolated therefrom with a combination of primers comprising a set of primers derived from stx1 and a set of primers derived from stx2 and detecting the presence or the absence of an amplification product for each set of primers of said combination.

7. The method of claim 1, further comprising detection of the espK gene, the Z6065 gene, and at least one gene selected from the group consisting of espy, ureD, Z2098, Z1151, Z1153, Z1154, Z1155, and Z1156.

8. The method of claim 2, further comprising performing a PCR assay on said food product or DNA isolated therefrom with a combination of primers comprising a set of primers derived from espK, a set of primers derived from Z6065, and a set of primers derived from at least one of espy, ureD, Z2098, Z1151, Z1153, Z1154, Z1155, and Z1156; and detecting the presence or the absence of an amplification product for each set of primers of said combination.

* * * * *

```
                         SEQUENCE LISTING

<160> NUMBER OF SEQ ID NOS: 79

<210> SEQ ID NO 1
<211> LENGTH: 334
<212> TYPE: DNA
<213> ORGANISM: Escherichia coli

<400> SEQUENCE: 1
gggtgttcta ccgcagggc ggggaattct aagtgatatc catcatcgca tccagtgcgc     60
ccggtttatc cccgctgatg cggggaacac agcggcacgc tggattgaac aaatccctgg    120
gccggtttat ccccgctggc gcgggaaca ctttatacac ggatcctgtg tgccgtggac     180
cgccggttta tccccgctgg cgcggggaac acgagctggc gatagccctg aatgaactgg    240
cagacggtta atccccgctg gcgcggggaa cacaaaccga acacacgat caatccgaat     300 atgagcggtt tatccccgct ggcgcgggga acac                                334

<210> SEQ ID NO 2
<211> LENGTH: 212
<212> TYPE: DNA
<213> ORGANISM: Escherichia coli

<400> SEQUENCE: 2
gggtgttcta ccgcagggc ggggaattct aagtgatatc catcatcgca tccagtgcgc     60
ccggtttatc cccgctgatg cggggaacac agcggcacgc tggattgaac aaatccctgg    120
gccggtttat ccccgctggc gcgggaaca caaaccgaaa cacacgatca atccgaatat    180
gagcggttta tccccgctgg cgcggggaac ac                                  212

<210> SEQ ID NO 3
<211> LENGTH: 212
<212> TYPE: DNA
<213> ORGANISM: Escherichia coli

<400> SEQUENCE: 3
gggtgttcta ccgcagggc ggggaattct aagtgatatc catcatcgca tccagtgcgc     60
ccggtttatc cccgctgatg cggggaacac agcggcacgc tggattgaac aaatccctgg    120
gccggtttat ccccgctggc gcgggaaca ctttggtgac agttttgtc actgttttgg     180 tgacggttta tccccgctgg cgcggggaac ac                                  212

<210> SEQ ID NO 4
<211> LENGTH: 273
<212> TYPE: DNA
<213> ORGANISM: Escherichia coli

<400> SEQUENCE: 4
gggtgttcta ccgcagggc ggggaattct aagtgatatc catcatcgca tccagtgcgc     60
ccggtttatc cccgctgatg cggggaacac agcggcacgc tggattgaac aaatccctgg    120
gccggtttat ccccgctggc gcgggaaca caaaccgaaa cacacgatca atccgaatat    180
gagcggttta tccccgctgg cgcggggaac actttggtga cagttttgt cactgttttg    240 gtgacggttt atccccgctg gcgcggggaa cac                                 273
```

<210> SEQ ID NO 5
<211> LENGTH: 272
<212> TYPE: DNA
<213> ORGANISM: Escherichia coli

<400> SEQUENCE: 5
tggtttatcc ccactggcgc ggggaacttg agccctgcca gaatgggggcc tctttttgtac    60 ccggtttatc cccgctgccg cggggaacac atttactgat tgtaccaggt aggaaaagat    120
cgcggtttat ccccgctggc gcggggaact catgattgtc gattttttcc gacaggattt    180
tgcggtttat ccccgctggc gcggggaact cgtcacactg ccgtgcatta ttacagccag    240
gcgcggttta tccccgctgg cgcggggaac tc    272

<210> SEQ ID NO 6
<211> LENGTH: 395
<212> TYPE: DNA
<213> ORGANISM: Escherichia coli

<400> SEQUENCE: 6
tggtttatcc ccgctggcgc ggggaactcg acagaacggc ctcagtagtc tcgtcaggct    60
ccggtttatc cccgctggcg cggggagctc tacgtgaaga atatttgcaa cacccgcaag    120
aacggtttat ccccgctggc gcggggaaca ctccaacctt ccatgagata cgcgcattag    180
cggcggttta tccccgctgg cgcggggaac accgtgaccg cctgtacacg ctgtaatggc    240
tcaccggttt atccccgctg gcgcggggaa cacacactat ccgggcggta ttacgcccaa    300
atatccggtt tatccccgct ggcgcgggga acacctgccg ggtgaaacca ctcgcggcag    360
atcttgcggt ttatccccgc tggcgcgggg aacac    395

<210> SEQ ID NO 7
<211> LENGTH: 334
<212> TYPE: DNA
<213> ORGANISM: Escherichia coli

<400> SEQUENCE: 7
gggagttcta ccgcaggggc ggggaattct aagtgatatc catcatcgca tccagtgcgc    60
ccggtttatc cccgctggcg cggggaacac tcacgcgctg ttacccagtc cctttttttc    120
agcggtttat ccccgctggc gcggggaaca ctacaggaaa gaatccgcca acggcgacag    180
gggcggttta tccccgctgg cgcggggaac acgaatatcc acccgtcctg tattccgcca    240
attgcggttt atccccgctg gcgcggggaa cactaccaaa ccggaatctt tccatataac    300
ggcggcggtt tatccccgct ggcgcgggga acac    334

<210> SEQ ID NO 8
<211> LENGTH: 273
<212> TYPE: DNA
<213> ORGANISM: Escherichia coli

<400> SEQUENCE: 8
gggagttcta ccgcaggggc ggggaattct aagtgatatc catcatcgca tccagtgcgc    60
ccggtttatc cccgctgacg cggggaacac aaaaccaaac ttctccataa attccatagc    120
cgcggtttat ccccgctggc gcggggaaca cgagtctatc agcgacacta ccggcaatag    180
cgacggttta tccccgctgg cgcggggaac acctatagcg ccacgttccg agcgctgcga    240
gctgcggttt atccccgctg gcgcggggaa cac    273

<210> SEQ ID NO 9
<211> LENGTH: 822
<212> TYPE: DNA
<213> ORGANISM: Escherichia coli

<400> SEQUENCE: 9

```
tggtttatcc ccgctggcac ggggaactcg cctgacattg cagacgttac aaattgagag      60
gcggtttatc cccgctggcg cggggaactc taatcacgtt ttagcgcgcc ctcgtccggt     120
ttcggtttat ccccgctggc gcggggaact catcttcttg ttcaggaacg tcagtagagg     180
tgtcggttta tccccgctgg cgcggggaac tcagcattaa ccccaccag ctcgacgtgt      240
gtggcggttt atccccgctg gcgcggggaa ctcgcgggcg ttaacgcggt gatactgttt     300
gacggcggtt tatccccgct ggcgcgggga actcaccgag cgccgctggg aggcgtatct     360
cacgttcggt ttatccccgc tggcgcgggg aactctgaat gatcggaaag acgctgcaaa     420
ggcaatgcgg tttatccccg ctggcgcggg gaactcatta aaggattatt tgatgagtc      480
tgaaaaatcg gttatcccc gctggcgcgcg gggaactctga ttttggtggc ggggtgact     540
ggggggaatac ggtttatccc cgctggcgcg gggaactcta ccggtgtgaa ttacagcacc    600
accgccaccc cggtttatcc ccgctggcgc ggggaactcc aaacaggtcg acatgtttgg    660
ctaacagcta acggtttatc cccgctggcg cggggaactc cgataacaca gggccgtcaa    720
tgcggcccctt ttcggtttat ccccgctggc gcggggaact cataccgggt tttgctccag    780
cagcgccagt tcctggttta tccccgctgg cgcggggaac tc                        822
```

<210> SEQ ID NO 10
<211> LENGTH: 578
<212> TYPE: DNA
<213> ORGANISM: Escherichia coli

<400> SEQUENCE: 10

```
tggtttatcc ccgctggcgc ggggagctca acatcggaaa cggcttcgcg gcggcggcgt      60
ccggtttatc cccgctggcg cggggaactc gacagaacgg cctcagtagt ctcgtcaggc     120
tccggtttat ccccgctggc gcggggagct ctacgtgaag aatatttgca acacccgcaa     180
gaacggtttta tccccgctgg cgcggggagc tcggcatagc caggctgatc cggcgacggc    240
cttacggttt atccccgctg gcgcggggaa cacaatcgtg tgtaaattcg cggcggctcc    300
actggcggtt tatccccgct ggcgcgggga acactggtcg aaatatagac agcatgttcc     360
gtaccacggt ttatccccgc tggcgcgggg aacacacact atccgggcgg tattacgccc    420
aaatatccgg tttatccccg ctggcgcggg gaacacctgc cgggtgaaac cactcgcggc     480
agatcttgcg gtttatcccc gctggcgcgg ggaacacact actgtcggta gctgggagga    540
tgaggagatc ggtttatccc cgctggcgcg gggaacac                             578
```

<210> SEQ ID NO 11
<211> LENGTH: 21
<212> TYPE: DNA
<213> ORGANISM: Escherichia coli

<400> SEQUENCE: 11

```
gggaacacaa accgaaacac a                                                21
```

<210> SEQ ID NO 12
<211> LENGTH: 19
<212> TYPE: DNA
<213> ORGANISM: Escherichia coli

```
<400> SEQUENCE: 12
cttagtgtgt tccccgcgc                                                19

<210> SEQ ID NO 13
<211> LENGTH: 24
<212> TYPE: DNA
<213> ORGANISM: Escherichia coli

<400> SEQUENCE: 13
gaacactttg gtgacagttt ttgt                                          24

<210> SEQ ID NO 14
<211> LENGTH: 19
<212> TYPE: DNA
<213> ORGANISM: Escherichia coli

<400> SEQUENCE: 14
cttagtgtgt tccccgcgc                                                19

<210> SEQ ID NO 15
<211> LENGTH: 21
<212> TYPE: DNA
<213> ORGANISM: Escherichia coli

<400> SEQUENCE: 15
gaacacaaac cgaaacacac g                                             21

<210> SEQ ID NO 16
<211> LENGTH: 22
<212> TYPE: DNA
<213> ORGANISM: Escherichia coli

<400> SEQUENCE: 16
ataaaccgtc accaaaacag tg                                            22

<210> SEQ ID NO 17
<211> LENGTH: 20
<212> TYPE: DNA
<213> ORGANISM: Escherichia coli

<400> SEQUENCE: 17
gaacttgagc cctgccagaa                                               20

<210> SEQ ID NO 18
<211> LENGTH: 21
<212> TYPE: DNA
<213> ORGANISM: Escherichia coli

<400> SEQUENCE: 18
accgcgatct tttcctacct g                                             21

<210> SEQ ID NO 19
<211> LENGTH: 18
<212> TYPE: DNA
<213> ORGANISM: Escherichia coli

<400> SEQUENCE: 19
gtgaccgcct gtacacgc                                                 18

<210> SEQ ID NO 20
<211> LENGTH: 21
<212> TYPE: DNA
<213> ORGANISM: Escherichia coli
```

-continued

```
<400> SEQUENCE: 20
cggatatttg ggcgtaatac c                                              21

<210> SEQ ID NO 21
<211> LENGTH: 19
<212> TYPE: DNA
<213> ORGANISM: Escherichia coli

<400> SEQUENCE: 21
ctgccgcgag tggtttcac                                                 19

<210> SEQ ID NO 22
<211> LENGTH: 22
<212> TYPE: DNA
<213> ORGANISM: Escherichia coli

<400> SEQUENCE: 22
cggggaacac tacaggaaag aa                                             22

<210> SEQ ID NO 23
<211> LENGTH: 21
<212> TYPE: DNA
<213> ORGANISM: Escherichia coli

<400> SEQUENCE: 23
ggcggaatac aggacgggtg g                                              21

<210> SEQ ID NO 24
<211> LENGTH: 21
<212> TYPE: DNA
<213> ORGANISM: Escherichia coli

<400> SEQUENCE: 24
gagtctatca gcgacactac c                                              21

<210> SEQ ID NO 25
<211> LENGTH: 18
<212> TYPE: DNA
<213> ORGANISM: Escherichia coli

<400> SEQUENCE: 25
aaccgcagct cgcagcgc                                                  18

<210> SEQ ID NO 26
<211> LENGTH: 18
<212> TYPE: DNA
<213> ORGANISM: Escherichia coli

<400> SEQUENCE: 26
ggaactcacc gagcgccg                                                  18

<210> SEQ ID NO 27
<211> LENGTH: 23
<212> TYPE: DNA
<213> ORGANISM: Escherichia coli

<400> SEQUENCE: 27
gcctttgcag cgtctttccg atc                                            23

<210> SEQ ID NO 28
<211> LENGTH: 22
<212> TYPE: DNA
```

<213> ORGANISM: Escherichia coli

<400> SEQUENCE: 28
acaatcgtgt gtaaattcgc gg                                    22

<210> SEQ ID NO 29
<211> LENGTH: 21
<212> TYPE: DNA
<213> ORGANISM: Escherichia coli

<400> SEQUENCE: 29
gataaaccgt ggtacggaac a                                     21

<210> SEQ ID NO 30
<211> LENGTH: 20
<212> TYPE: DNA
<213> ORGANISM: Escherichia coli

<400> SEQUENCE: 30
tgaaaccact cgcggcagat                                       20

<210> SEQ ID NO 31
<211> LENGTH: 22
<212> TYPE: DNA
<213> ORGANISM: Escherichia coli

<400> SEQUENCE: 31
ataaaccgat ctcctcatcc tc                                    22

<210> SEQ ID NO 32
<211> LENGTH: 23
<212> TYPE: DNA
<213> ORGANISM: Escherichia coli

<400> SEQUENCE: 32
cgatcaatcc gaatatgagc ggt                                   23

<210> SEQ ID NO 33
<211> LENGTH: 24
<212> TYPE: DNA
<213> ORGANISM: Escherichia coli

<400> SEQUENCE: 33
cactgttttg gtgacggttt atcc                                  24

<210> SEQ ID NO 34
<211> LENGTH: 24
<212> TYPE: DNA
<213> ORGANISM: Escherichia coli

<400> SEQUENCE: 34
acaaaaactg tcaccaaagt gttc                                  24

<210> SEQ ID NO 35
<211> LENGTH: 21
<212> TYPE: DNA
<213> ORGANISM: Escherichia coli

<400> SEQUENCE: 35
tggggcctct tttgtacccg g                                     21

<210> SEQ ID NO 36
<211> LENGTH: 25

<212> TYPE: DNA
<213> ORGANISM: Escherichia coli

<400> SEQUENCE: 36
tgtaatggct caccggttta tcccc                                             25

<210> SEQ ID NO 37
<211> LENGTH: 20
<212> TYPE: DNA
<213> ORGANISM: Escherichia coli

<400> SEQUENCE: 37
tccgccaacg gcgacagggg                                                   20

<210> SEQ ID NO 38
<211> LENGTH: 22
<212> TYPE: DNA
<213> ORGANISM: Escherichia coli

<400> SEQUENCE: 38
tcggaacgtg gcgctatagg tg                                                22

<210> SEQ ID NO 39
<211> LENGTH: 25
<212> TYPE: DNA
<213> ORGANISM: Escherichia coli

<400> SEQUENCE: 39
ctgggaggcg tatctcacgt tcggt                                             25

<210> SEQ ID NO 40
<211> LENGTH: 27
<212> TYPE: DNA
<213> ORGANISM: Escherichia coli

<400> SEQUENCE: 40
tgctgtctat atttcgacca gtgttcc                                           27

<210> SEQ ID NO 41
<211> LENGTH: 25
<212> TYPE: DNA
<213> ORGANISM: Escherichia coli

<400> SEQUENCE: 41
ccagctaccg acagtagtgt gttcc                                             25

<210> SEQ ID NO 42
<211> LENGTH: 26
<212> TYPE: DNA
<213> ORGANISM: Escherichia coli

<400> SEQUENCE: 42
gcagrcatca aaagcgaaat cacacc                                            26

<210> SEQ ID NO 43
<211> LENGTH: 26
<212> TYPE: DNA
<213> ORGANISM: Escherichia coli

<400> SEQUENCE: 43
tcgtttggta actgtggcag atactc                                            26

<210> SEQ ID NO 44

-continued

<210> SEQ ID NO 44
<211> LENGTH: 23
<212> TYPE: DNA
<213> ORGANISM: Escherichia coli

<400> SEQUENCE: 44
tcaggttcct cgtctgatgc cgc                                          23

<210> SEQ ID NO 45
<211> LENGTH: 23
<212> TYPE: DNA
<213> ORGANISM: Escherichia coli

<400> SEQUENCE: 45
ctggttcagg cctggagcag tcc                                          23

<210> SEQ ID NO 46
<211> LENGTH: 22
<212> TYPE: DNA
<213> ORGANISM: Escherichia coli

<400> SEQUENCE: 46
gcaataattg actctgattg cc                                           22

<210> SEQ ID NO 47
<211> LENGTH: 21
<212> TYPE: DNA
<213> ORGANISM: Escherichia coli

<400> SEQUENCE: 47
gctgctgcgg taaaatttac t                                            21

<210> SEQ ID NO 48
<211> LENGTH: 21
<212> TYPE: DNA
<213> ORGANISM: Escherichia coli

<400> SEQUENCE: 48
ctgaaaagag ccagaacgtg c                                            21

<210> SEQ ID NO 49
<211> LENGTH: 22
<212> TYPE: DNA
<213> ORGANISM: Escherichia coli

<400> SEQUENCE: 49
tgcctaagat cattacccgg ac                                           22

<210> SEQ ID NO 50
<211> LENGTH: 24
<212> TYPE: DNA
<213> ORGANISM: Escherichia coli

<400> SEQUENCE: 50
cgatcattgt gggcatgtta tgcc                                         24

<210> SEQ ID NO 51
<211> LENGTH: 22
<212> TYPE: DNA
<213> ORGANISM: Escherichia coli

<400> SEQUENCE: 51
cctgaattca cacggtgatg cg                                           22

```
<210> SEQ ID NO 52
<211> LENGTH: 27
<212> TYPE: DNA
<213> ORGANISM: Escherichia coli

<400> SEQUENCE: 52 gccttttat gttcattatt gcggttg                                          27

<210> SEQ ID NO 53
<211> LENGTH: 26
<212> TYPE: DNA
<213> ORGANISM: Escherichia coli

<400> SEQUENCE: 53
gtatagtttt agcaataacct tcctgc                                         26

<210> SEQ ID NO 54
<211> LENGTH: 21
<212> TYPE: DNA
<213> ORGANISM: Escherichia coli

<400> SEQUENCE: 54
gattgtggcg attaatgggg g                                               21

<210> SEQ ID NO 55
<211> LENGTH: 21
<212> TYPE: DNA
<213> ORGANISM: Escherichia coli

<400> SEQUENCE: 55
acaccgatct ggtcattggc g                                               21

<210> SEQ ID NO 56
<211> LENGTH: 23
<212> TYPE: DNA
<213> ORGANISM: Escherichia coli

<400> SEQUENCE: 56
aaacgccttt aaaatctgcg tct                                             23

<210> SEQ ID NO 57
<211> LENGTH: 21
<212> TYPE: DNA
<213> ORGANISM: Escherichia coli

<400> SEQUENCE: 57
tgccgtgcgc acagtcataa g                                               21

<210> SEQ ID NO 58
<211> LENGTH: 20
<212> TYPE: DNA
<213> ORGANISM: Escherichia coli

<400> SEQUENCE: 58
gcccatggct ccacatcctg                                                 20

<210> SEQ ID NO 59
<211> LENGTH: 26
<212> TYPE: DNA
<213> ORGANISM: Escherichia coli

<400> SEQUENCE: 59
ccaaaaaagt tatgatgatt gcactg                                          26
```

<210> SEQ ID NO 60
<211> LENGTH: 23
<212> TYPE: DNA
<213> ORGANISM: Escherichia coli

<400> SEQUENCE: 60
gcactggccc ttgttgctca ggc                                    23

<210> SEQ ID NO 61
<211> LENGTH: 27
<212> TYPE: DNA
<213> ORGANISM: Escherichia coli

<400> SEQUENCE: 61
gctcttccag tgagaatgtc tttccgg                                27

<210> SEQ ID NO 62
<211> LENGTH: 29
<212> TYPE: DNA
<213> ORGANISM: Escherichia coli

<400> SEQUENCE: 62
tttgtyactg tsacagcwga agcyttacg                              29

<210> SEQ ID NO 63
<211> LENGTH: 26
<212> TYPE: DNA
<213> ORGANISM: Escherichia coli

<400> SEQUENCE: 63
ccccagttca rwgtragrtc macrtc                                 26

<210> SEQ ID NO 64
<211> LENGTH: 26
<212> TYPE: DNA
<213> ORGANISM: Escherichia coli

<400> SEQUENCE: 64
attcagatag aagaagcgcg ggccag                                 26

<210> SEQ ID NO 65
<211> LENGTH: 28
<212> TYPE: DNA
<213> ORGANISM: Escherichia coli

<400> SEQUENCE: 65
cttgcaacac gttacgctgc cgagtatt                               28

<210> SEQ ID NO 66
<211> LENGTH: 24
<212> TYPE: DNA
<213> ORGANISM: Escherichia coli

<400> SEQUENCE: 66
tacgctgatc accatgcctg gtgc                                   24

<210> SEQ ID NO 67
<211> LENGTH: 22
<212> TYPE: DNA
<213> ORGANISM: Escherichia coli

<400> SEQUENCE: 67
taactgctat acctccgcgc cg                                     22

<210> SEQ ID NO 68
<211> LENGTH: 27
<212> TYPE: DNA
<213> ORGANISM: Escherichia coli

<400> SEQUENCE: 68
tgtaacaccc agacggtcag caacatg        27

<210> SEQ ID NO 69
<211> LENGTH: 29
<212> TYPE: DNA
<213> ORGANISM: Escherichia coli

<400> SEQUENCE: 69
tcacttccag tttctggtga tgttttgat      29

<210> SEQ ID NO 70
<211> LENGTH: 31
<212> TYPE: DNA
<213> ORGANISM: Escherichia coli

<400> SEQUENCE: 70
tgggtgaggt taaaatataa agaacgattg c   31

<210> SEQ ID NO 71
<211> LENGTH: 31
<212> TYPE: DNA
<213> ORGANISM: Escherichia coli

<400> SEQUENCE: 71
taagatattt tctgactttc cgcatgcgct t   31

<210> SEQ ID NO 72
<211> LENGTH: 25
<212> TYPE: DNA
<213> ORGANISM: Escherichia coli

<400> SEQUENCE: 72
aaagagccag cgcagagctg accag          25

<210> SEQ ID NO 73
<211> LENGTH: 23
<212> TYPE: DNA
<213> ORGANISM: Escherichia coli

<400> SEQUENCE: 73
ttcgctggaa gcagagcccg tgc            23

<210> SEQ ID NO 74
<211> LENGTH: 31
<212> TYPE: DNA
<213> ORGANISM: Escherichia coli

<400> SEQUENCE: 74
ctggatgatc tcagtgggcg ttcttatgta a   31

<210> SEQ ID NO 75
<211> LENGTH: 27
<212> TYPE: DNA
<213> ORGANISM: Escherichia coli

<400> SEQUENCE: 75

```
tcgtcaggca ctgtctgaaa ctgctcc                                    27

<210> SEQ ID NO 76
<211> LENGTH: 24
<212> TYPE: DNA
<213> ORGANISM: Escherichia coli

<400> SEQUENCE: 76
ggtgaaggag ytggcgaagg cgtc                                       24

<210> SEQ ID NO 77
<211> LENGTH: 23
<212> TYPE: DNA
<213> ORGANISM: Escherichia coli

<400> SEQUENCE: 77
ccggtggatt tggatgggtt acg                                        23

<210> SEQ ID NO 78
<211> LENGTH: 22
<212> TYPE: DNA
<213> ORGANISM: Escherichia coli

<400> SEQUENCE: 78
tgtgaacctc tctggcatgg ag                                         22

<210> SEQ ID NO 79
<211> LENGTH: 24
<212> TYPE: DNA
<213> ORGANISM: Escherichia coli

<400> SEQUENCE: 79
taaagttggt agattgtgac tggc                                       24
```